United States Patent
Cabib et al.

[11] Patent Number: 5,991,028
[45] Date of Patent: *Nov. 23, 1999

[54] SPECTRAL BIO-IMAGING METHODS FOR CELL CLASSIFICATION

[75] Inventors: Dario Cabib, Timrat; Robert A. Buckwald, Ramat Yishai; Zvi Malik, Kfar Haroe; Nissim Ben-Yosef, Jerusalem, all of Israel

[73] Assignee: Applied Spectral Imaging Ltd., Migdal Haemek, Israel

[*] Notice: This patent is subject to a terminal disclaimer.

[21] Appl. No.: 08/824,234

[22] Filed: Mar. 25, 1997

Related U.S. Application Data

[62] Continuation-in-part of application No. 08/571,047, Dec. 12, 1995, Pat. No. 5,784,162, which is a continuation-in-part of application No. 08/392,019, Feb. 21, 1995, Pat. No. 5,539,517, which is a continuation-in-part of application No. 08/107,673, filed as application No. PCT/US92/01171, Feb. 19, 1992, abandoned.

[30] Foreign Application Priority Data

Feb. 22, 1991 [IL] Israel ............................................ 97328

[51] Int. Cl.⁶ ............................................................. G01B 9/02
[52] U.S. Cl. ........................................... 356/346; 382/133
[58] Field of Search ........................................... 356/346, 300, 356/319, 326; 250/339.07, 339.08, 339.11, 341.8; 435/1, 7.23; 382/128, 133

[56] References Cited

U.S. PATENT DOCUMENTS 5,440,388   8/1995   Erickson ................................. 356/349

Primary Examiner—Samuel A. Turner
Attorney, Agent, or Firm—Mark M. Friedman

[57] ABSTRACT

According to the present invention there is provided a spectral bio-imaging methods which can be used for automatic and/or semiautomatic spectrally resolved morphometric classification of cells, the method comprising the steps of (a) preparing a sample to be spectrally imaged, the sample including at least a portion of at least one cell; (b) viewing the sample through an optical device, the optical device being optically connected to an imaging spectrometer, the optical device and the imaging spectrometer being for obtaining a spectrum of each pixel of the sample; (c) classifying each of the pixels into classification groups according to the pixels spectra; and (d) analyzing the classification groups and thereby classifying the at least one cell into a cell class.

22 Claims, 13 Drawing Sheets

(7 of 13 Drawing Sheet(s) Filed in Color)

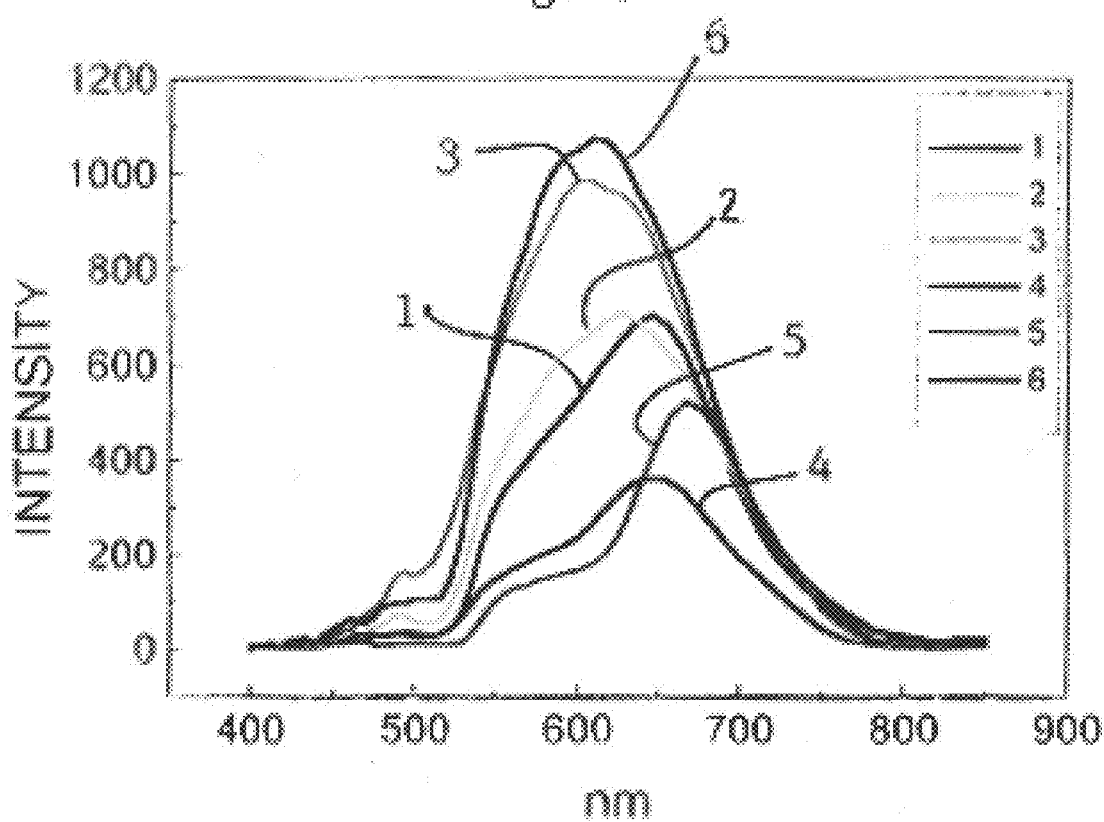

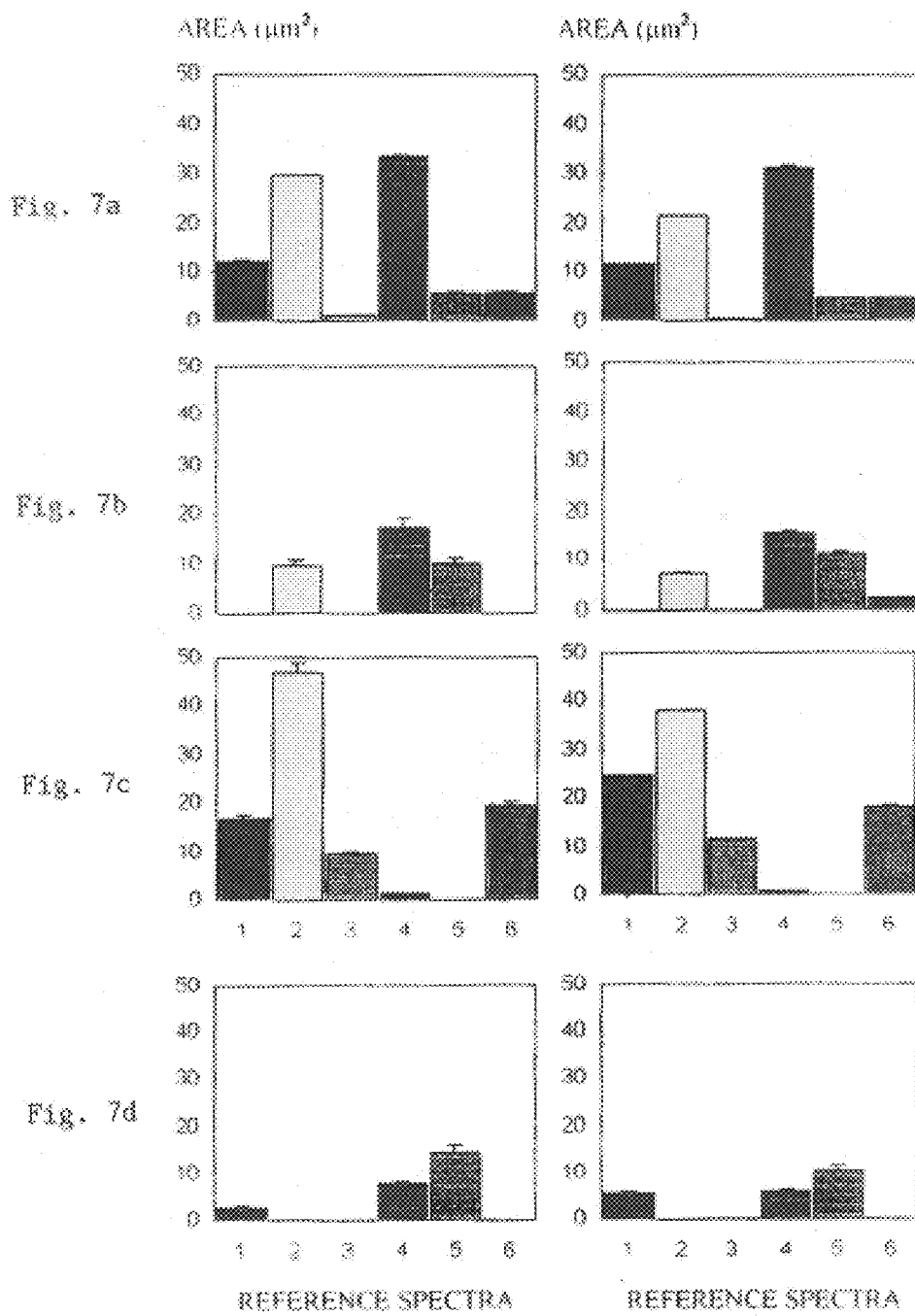

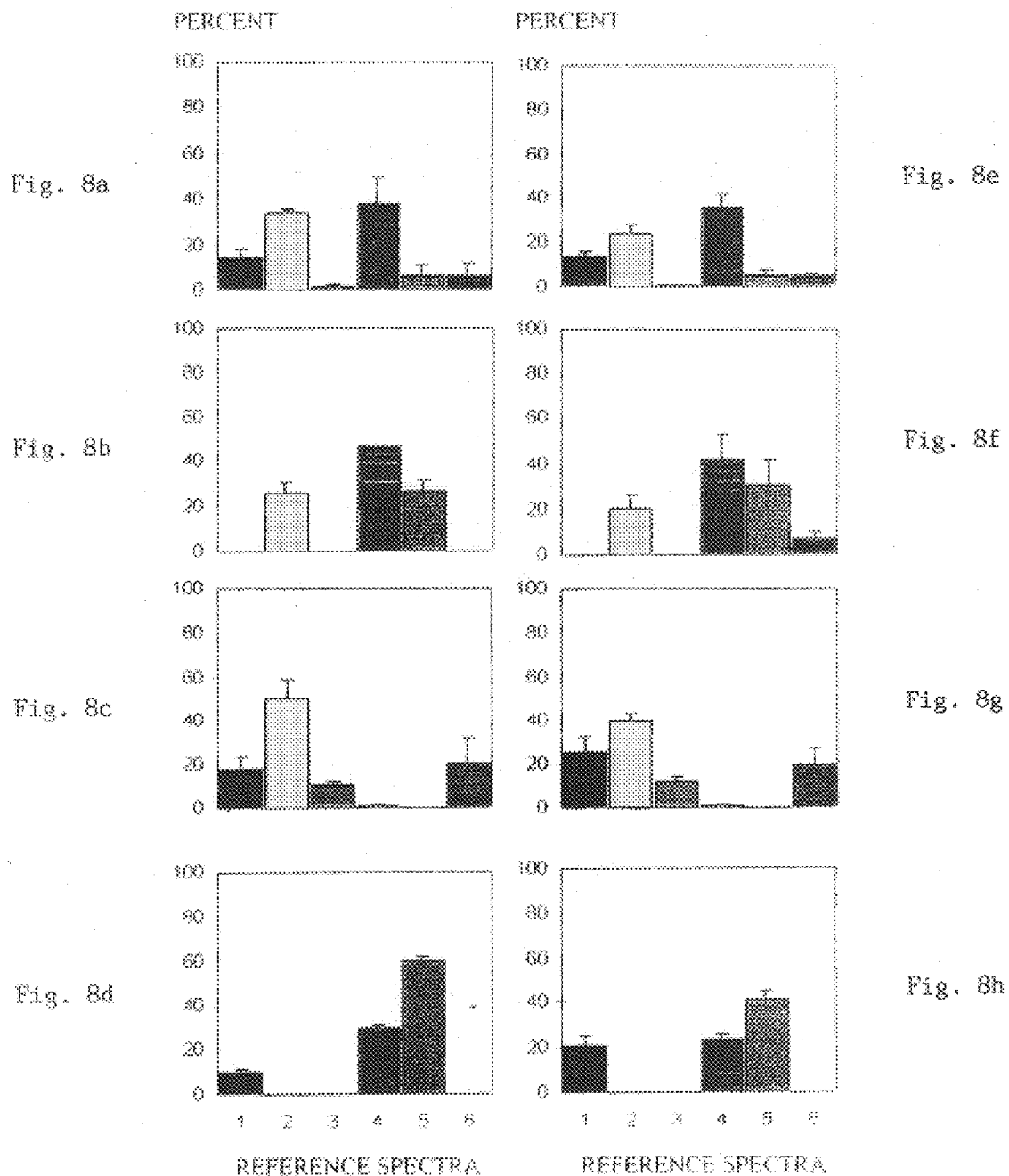

Fig. 9a
Fig. 9b
Fig. 9c
Fig. 9d
Fig. 9e
Fig. 9f
Fig. 9g
Fig. 9h
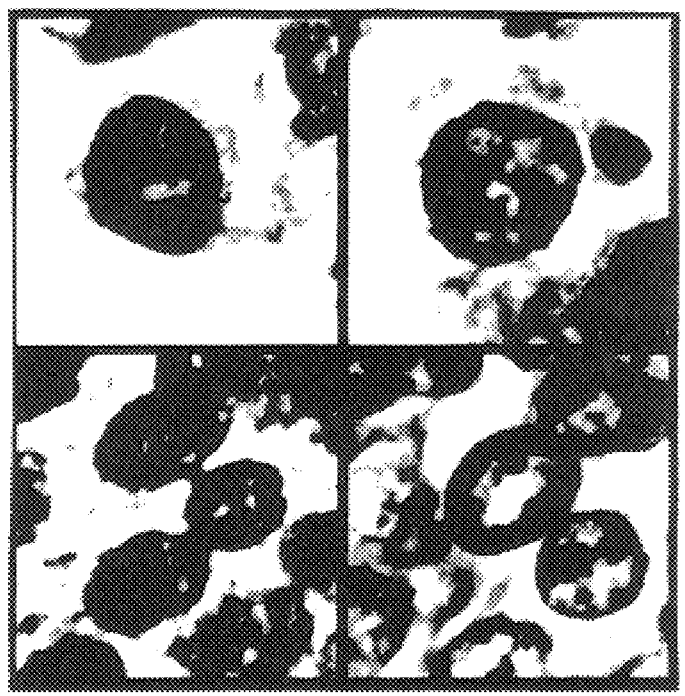
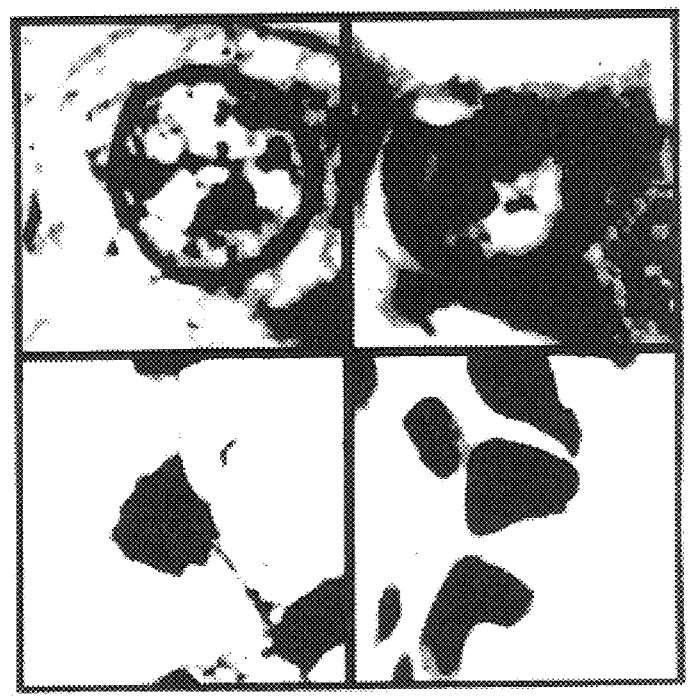

OPTICAL DENSITY

OPTICAL DENSITY

SPECTRAL BIO-IMAGING METHODS FOR CELL CLASSIFICATION

This is a continuation-in-part of U.S. patent application Ser. No. 08/571,047, filed Dec. 12, 1995, is now U.S. Pat. No. 5,784,162 which is a continuation-in-part of U.S. patent application Ser. No. 08/392,019 filed Feb. 21, 1995, now U.S. Pat. No. 5,539,517, issued Jul. 23, 1996, which is a continuation-in-part of U.S. patent application Ser. No. 08/107,673, filed Aug. 18, 1993, now abandoned, which is a 371 of PCT/US92/01171, filed Feb. 19, 1992.

FIELD AND BACKGROUND OF THE INVENTION

The present invention relates to spectral methods in general and, more particularly, to spectral imaging methods for cell classification, biological research, medical diagnostics and therapy, which methods are referred to hereinbelow as spectral bio-imaging methods. The spectral bio-imaging methods of the invention can be used to provide automatic and/or semiautomatic spectrally resolved morphometric classification (e.g., detection, grading) of neoplasm. Specifically, the methods can be used to detect the spatial organization and to qualify and quantify cellular and tissue constituents and structures associated with, for example, tumorogenesis, using, for example, light transmission microscopy combined with high spatial and spectral resolutions. Furthermore, the methods of the present invention can be used to detect cellular spatial organization and to quantify cellular and tissue natural constituents, domains and structures using light transmission, reflection, scattering and fluorescence emission strategies, with high spatial and spectral resolutions, and may therefore be employed for classification of cancer cells using what is referred herein as spectrally resolved morphometry. In particular the methods of the present invention can be used for classification of cells to developmental stages, and to qualify and quantify metabolic processes within cells. The method can further be used to develop new and more fine tuned indexes for neoplasm classification (including grading), which will eventually replace the existing indexes.

A spectrometer is an apparatus designed to accept light, to separate (disperse) it into its component wavelengths, and measure the lights spectrum, that is the intensity of the light as a function of its wavelength. An imaging spectrometer is one which collects incident light from a scene and measures the spectra of each pixel (i.e., picture element) thereof.

Spectroscopy is a well known analytical tool which has been used for decades in science and industry to characterize materials and processes based on the spectral signatures of chemical constituents. The physical basis of spectroscopy is the interaction of light with matter. Traditionally, spectroscopy is the measurement of the light intensity emitted, transmitted, scattered or reflected from a sample, as a function of wavelength, at high spectral resolution, but without any spatial information.

Spectral imaging, on the other hand, is a combination of high resolution spectroscopy and high resolution imaging (i.e., spatial information). Most of the works so far described concern either obtaining high spatial resolution information from a biological sample yet providing only limited spectral information, for example, when high spatial resolution imaging is performed with one or several discrete band-pass filters [See, Andersson-Engels el al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

Conceptually, a spectral bio-imaging system consists of (i) a measurement system, and (ii) an analysis software. The measurement system includes all of the optics, electronics and the manner in which the sample is illuminated (e.g., light source selection), the mode of measurement (e.g., fluorescence or transmission), as well as the calibration best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features. However, the high cost, size and configuration of remote sensing spectral imaging systems (e.g., Landsat, AVIRIS) has limited their use to air and satellite-born applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30]

There are three basic types of spectral dispersion methods that might be considered for a spectral bio-imaging system: (i) spectral grating or prism, (ii) spectral filters and (iii) interferometric spectroscopy. As will be described below, the latter is best suited to implement the method of the present invention, yet as will be appreciated by one ordinarily skilled in the art, grating, prism and filters based spectral bio-imaging systems may also be found useful in some applications.

In a grating or prism (i.e., monochromator) based systems, also known as slit-type imaging spectrometers, such as for example the DILOR system: [see, Valisa et al. (September 1995) presentation at the SPIE Conference European Medical Optics Week, BiOS Europe '95, Barcelona, Spain], only one axis of a CCD (charge coupled device) array detector (the spatial axis) provides real imagery data, while a second (spectral) axis is used for sampling the intensity of the light which is dispersed by the grating or prism as function of wavelength. The system also has a slit in a first focal plane, limiting the field of view at any given time to a line of pixels. Therefore, a full image can only be obtained after scanning the grating (or prism) or the incoming beam in a direction parallel to the spectral axis of the CCD in a method known in the literature as line scanning. The inability to visualize the two-dimensional image before the whole measurement is completed, makes it impossible to choose, prior to making the measurement, a desired region of interest from within the field of view and/or to optimize the system focus, exposure time, etc. Grating and prism based spectral imagers are in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-tonoise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using acousto-optic tunable filters (AOTF) or liquid-crystal tunable filter (LCTF), see below. Similarly to the slit type imaging spectrometers equipped with a grating or prism as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD.

Tunable filters, such as AOTFs and LCTFs have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning, demanding careful and complicated registration procedures thereafter.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

A method and apparatus for spectral analysis of images which have advantages in the above respects was disclosed in U.S. patent application Ser. No. 08/392,019 to Cabib et al., filed Feb. 21st, 1995, now U.S. Pat. No. 5,539,517, issued Jul. 23, 1996, which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed.

Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measuring time and/or substantially increasing the signal-to-noise ratio (i.e., sensitivity). The sensitivity advantage that interferometric spectroscopy has over the filter and grating or prism methods is known in the art as the multiplex or Fellgett advantage [see, Chamberlain (1979) The principles of interferometric spectroscopy, John Wiley and Sons, pp. 16–18 and p. 263].

Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$. However, whereas in the conventional grating or prism method the energy seen by every detector at any time is of the order of 1/n of the total, because the wavelength resolution is 1/n of the range, in a method according to the invention described in U.S. patent application Ser. No. 08/392,019 the energy is of the order of unity, because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. Pat. No. 5,539,517, all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fundus cameras for retinal imaging, fiber optics and endoscopes for industrial monitoring and medical imaging, diagnosis, therapy and others.

In a continuation application (U.S. patent application Ser. No. 08/571,047 to Cabib et al., filed Dec. 12, 1995, which is incorporated by reference as if fully set forth herein) the objective is to provide spectral imaging methods for biological research, medical diagnostics and therapy, which methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions. In U.S. patent application Ser. No. 08/571, 047, the use of the spectral imaging apparatus described in U.S. Pat. No. 5,539,517 for interphase fluorescent in situ hybridization of as much as six loci specific probes (each loci located on a different chromosome) was demonstrated, as well as additional biological and medical applications.

Spectral bio-imaging systems are potentially useful in all applications in which subtle spectral differences exist between chemical constituents whose spatial distribution and organization within an image are of interest. The measurement can be carried out using virtually any optical system attached to the system described in U.S. Pat. No. 5,539,517, for example, an upright or inverted microscope, a fluorescence microscope, a macro lens, an endoscope and a fundus camera. Furthermore, any standard experimental method can be used, including light transmission (bright field and dark field), auto-fluorescence and fluorescence of administered probes, etc.

Fluorescence measurements can be made with any standard filter cube (consisting of a barrier filter, excitation filter and a dichroic mirror), or any customized filter cube for special applications, provided the emission spectra fall within the spectral range of the system sensitivity. Spectral bio-imaging can also be used in conjunction with any standard spatial filtering method such as dark field and phase contrast, and even with polarized light microscopy. The effects on spectral information when using such methods must, of course, be understood to correctly interpret the measured spectral images.

In the evaluation of infiltrating breast carcinomas, ductal and lobular carcinomas may present similar histological appearances [Azzopardi J G, Chepick O F, Hartmann W H, Jafarey N A, Lombart-Bosch A, Ozello L (1982). The World Health Organization histological typing of breast tumors. 2nd ed. Am J Clin Pathol 78:806–816]. Some quantitative histopathological variables have been identified by morphological methods as an aid to the differentiation between ductal and lobular carcinomas [Ladekarl M and Sorensen F B (1993). Quantitive histopathological variables in in situ and invasive ductal carcinoma of the breast. AMPIS 101 (12):895–903]. The attempts to grade and to differentiate, or in other words to classify the tumors have been based mainly on nuclear morphology and chromatin structure [Ladekarl M and Sorensen F B (1993). Quantitive histopathological variables in in situ and invasive ductal carcinoma of the breast. AMPIS 101(12):895–903; Cornelisse C J, de Konig H R, Moolenaar A J (1984). Image and flow cytometric analysis of DNA content in breast cancer; relation to estrogen receptor content and lymph node involvement. Anal Quant Cytol Histol 4:9–18; Stenkvist B, Westman-Naeser S, Holmquist J (1978). Computerized nuclear morphology as an objective method for characterizing human cancer cell populations. Cancer Res 38:4688–4977; Dawson A E, Austin R E, Weinberg D S (1991). Nuclear grading of breast carcinoma by image analysis. Classification by multivariate and neural network analysis. Am J Clin Pathol 95:S29–S37]. Morphometric classification of other tumor types, such as but not limited to leukemias, lymphomas, sarcomas and other carcinomas [see, for example, Clarke A M, Reid W A and Jack A S (1993) Combined proliferating cell nuclear antigen and morphometric analysis in the diagnosis of cancerous lymphoid infiltrates. J. Clin. Pathol. 46:129–134] are also vastly implemented both in research medical practice.

Nevertheless, as was recently published following an NIH workshop which evaluated the reliability of histopathological diagnosis by the best pathologists in the field of cancer diagnostics, there is a discordance among expert pathologists in the diagnosis of neoplasm. Based on this workshop, it was concluded that histopathological decisionmaking is 100% subjective, regardless of the origin of specimen and that this state of affairs in histopathological diagnosis is not confined to a specific tumor, but is applicable to differential diagnosis in every organ. These conclusions were published in an editorial by A Bernard Ackerman (1996) entitled "Discordance among expert pathologists in diagnosis of melanocytic neoplasm", in Human pathology 27:1115–1116.

Close to 80% of breast carcinomas are of the ductal type [Aaltomaa S, Lipponen P: Prognostic factors in breast cancer (reviews). Int J Oncol 1:153, 1992; Toikkanen S, Jensuu H (1990). Prognostic factors and long-term survival in breast cancer in a defined urban population. APMIS 98:1005–1014]. The differentiation between ductal and lobular carcinomas has proven to be useful for evaluation of patient prognosis and determination of treatment [Ellis I O, Galea M, Broughton N, Locker A, Blaney R W and Elston C W (1992). Pathological prognostic factors in breast cancer: II Histological type; relationship with survival in a large study with long term follow-up. Histopathology 20:479–489; Eskelinen M, Lipponen P, Papinaho S, Aaltomaa S, IKosma V M, Klemi P (1992). DNA flow cytometry, nuclear morphometry, mitotic indices and steroid receptors as independent prognostic factors in female breast cancer. Int J Cancer 51:555–561; and Toikkanen S, Jensuu H (1990). Prognostic factors and long-term survival in breast cancer in a defined urban population. APMIS 98:1005–1014]. The tumors have some differences in clinical behavior and in the pattern of metastasis; lobular carcinoma is more multifocal and bilateral than ductal carcinoma [Azzopardi J G, Chepick O F, Hartmann W H, Jafarey N A, Lombart-Bosch A, Ozello L (1982). The World Health Organization histological typing of breast tumors. 2nd ed. Am J Clin Pathol 78:806–816], and patient survival expectancy is usually better [DiConstanzo D, Rosen P P, Gareen I, Franklin S, Lesser M (1990). Prognosis in infiltrating lobular carcinoma: an analysis of "classical" and variant tumors. Am J Surg Pathol 14:12–23; du Toit R S, Locker A P, Ellis I O, Elston C W, Nicholson R I, Robertson J F R (1991). An evaluation of differences in prognosis, recurrence patterns and receptor status between invasive lobular and other invasive carcinomas of the breast. Eur J Surg Oncol 17:251–257]. The two tumor types are morphologically different, cells of infiltrating lobular carcinoma are usually smaller than those of ductal carcinoma, less pleomorphic and have fewer mitotic figures. Infiltrating ductal carcinoma cells have more prominent nucleoli [Azzopardi J G, Chepick O F, Hartmann W H, Jafarey N A, Lombart-Bosch A, Ozello L (1982). The World Health Organization histological typing of breast tumors. 2nd ed. Am J Clin Pathol 78:806–816].

Some histological types of intraductal carcinoma have been recognized: comedo, cribriform, micropapillary and solid. All are recognized and classified by specific criteria and subdivided primarily by architectural pattern, cellular pleomorphism, and nuclear hyperchromasia [Page D L, Anderson T G (1987). Diagnostic histopathology of the breast. Edinburgh, Scotland: Churchill Livingstone, 120–157; Lagios M D (1990). Duct carcinoma in situ pathology and treatment. Surg Clin North Am 70:853–871; and Lennington W J, Jensen R A, Dalton L W, Page D L: Ductal carcinoma in situ of the breast: Heterogeneity of individual lesions. Cancer 73:118–124, 1994]. The survival expectancy for lobular carcinomas is usually better than that of ductal carcinomas [DiConstanzo D, Rosen P P, Gareen I, Franklin S, Lesser M (1990). Prognosis in infiltrating lobular carcinoma: an analysis of "classical" and variant tumors. Am J Surg Pathol 14:1223; du Toit R S, Locker A P, Ellis I O, Elston C W, Nicholson R I, Robertson J F R (1991). An evaluation of differences in prognosis, recurrencee patterns and receptor status between invasive lobular and other invasive carcinomas of the breast. Eur J Surg Oncol 17:251–257]. Lobular carcinomas are more often bilateral and multifocal [Ladekarl M, Sorensen F B: Prognostic, quantitive histopathologic variables in lobular carcinoma of the breast. Cancer 72:2602, 1993] and the pattern of metastasis from the tumors was found to be different. Unfortunately, histological classification of breast carcinomas is subjected to low reproducibility and attempts to classify morphological subtypes of lobular carcinomas with different prognoses, therefore seem futile [Ladekarl M, Sorensen F B: Prognostic, quantitive histopathologic variables in lobular carcinoma of the breast. Cancer 72:2602, 1993]. Both lobular and ductal types are now thought to arise from the terminal duct-lobular unit.

Characterization of nuclear features by different techniques is used for determination of diagnosis, treatment and prognosis. Quantitative estimation of various histopathological parameters such as two dimensional estimates of nuclear profile area, nuclear profile densities and mitotic profile numbers have been shown to correlate with differentiation and prognosis. Alterations in nuclear structure are the morphologic hallmark of cancer diagnosis. Nuclear size, shape, chromatin pattern have all been reported to change in breast cancer [Pienta K J, Coffey D S: Correlation of nuclear morphometry with progression of breast cancer. Nuclear Morphometry of breast cancer 2012, 1991]. However, heterogeneity in morphology and biology of tumors belonging to the same classification group has been found to be the most prominent feature of breast cancer [Komitowski D D and Janson C P (1990). Quantitative features of chromatin structure in the prognosis of breast cancer. Cancer 65:2725–2730].

Among 11 cytological parameters that were examined by de-las-Morenas et al. [de-las-Morenas A, Crespo P, Moroz K and Donnely M M (1995). Cytologic diagnosis of ductal versus lobular carcinoma of the breast. Acta Cytol 39(5) :865–869] using an automated morphometric system on cytologic specimens, chromatic pattern, nuclear size and overall cell size were found to be statistically different between infiltrating lobular and infiltrating ductal carcinoma cell nuclei. Thus, the presence of coarsely granular chromatin, nuclear size of more than 44 $\mu m^2$ and cell size of more than 82 $\mu m^2$, were found to be related to ductal carcinoma.

Ladekarl and Sorensen found that the main three-dimensional nuclear size, the main nuclear profile area and the mitotic index were all significantly larger in ductal than in lobular carcinomas, whereas the main nuclear density index was smaller in ductal carcinoma [Ladekarl M, Sorensen F B: Prognostic, quantitive histopathologic variables in lobular carcinoma of the breast. Cancer 72:2602, 1993]. Yu et al. also identified some distinct nuclear features useful in the differentiation of infiltrating ductal and lobular carcinoma [Yu G H, Sneige N, Kidd L D, Johnston and Katz R L (1995). Image analysis derived morphometric differences in fine needle aspirated of ductal and lobular breast carcinoma. Anal Quant Cytol Histol 17(2):88–92].

All these methods, however, employ only image (i.e., spatial) information for analysis. A whole new dimension of analysis may be added using spectral information which reflects the interaction between light and matter. The combination of both spatial and spectral information will largely contribute to cancer detection and classification.

There is thus a widely recognized need for, and it would be highly advantageous to have, spectral bio-imaging methods and spectral morphometric methods for cells classification devoid of the above described limitations, especially the subjectiveness of pathologists in neoplasm diagnosis, which provide advanced and quantitative, semi or fully automatic, means for cancer classification.

SUMMARY OF THE INVENTION

According to the present invention there are provided spectral bio-imaging methods which can be used for automatic and/or semiautomatic spectrally resolved morphometric classification (e.g., grading) of cells (e.g., neoplasm). The methods can also be used for classification of cells into grades, developmental stages, and to qualify and quantify metabolic processes within cells. The method can further be used to develop new and more fine tuned indexes for neoplasm and embryonic cells classification.

According to further features in preferred embodiments of the invention described below, the method comprising the steps of (a) preparing a sample to be spectrally imaged, the sample including at least a portion of at least one cell; (b) viewing the sample through an optical device, the optical device being optically connected to an imaging spectrometer, the optical device and the imaging spectrometer being for obtaining a spectrum of each pixel of the sample; (c) classifying each of the pixels into classification groups according to the pixels spectra; and (d) analyzing the classification groups and thereby classifying the at least one cell into a cell class.

According to still further features in the described preferred embodiments the preparation of step (a) involves staining the cell via a staining method selected from the group consisting of Haematoxylin-Eosin staining, Giemsa staining, mason tricolor and papanicolaou.

According to still further features in the described preferred embodiments the obtainment of the spectrum of each pixel of step (b) is effected by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) scanning (e.g., rotating or translating) one or more of the elements of the interferometer system (e.g., the interferometer as a whole), so that the optical path difference between the two coherent beams generated by the interferometer system is scanned simultaneously for all the pixels of the sample; and (v) recording signals of each of the detector elements as function of time using a recording device to form a spectral cube of data.

According to still further features in the described preferred embodiments the optical device is a microscope.

According to still further features in the described preferred embodiments the imaging spectrometer includes an element selected from the group consisting of a dispersion element, a filter and an interferometer.

According to still further features in the described preferred embodiments pixels classified to a classification group via the classification of step (c) are presented in an image by a preselected artificial color.

According to still further features in the described preferred embodiments pixels classified to a classification group via the classification of step (c) are presented as an abundance histogram.

According to still further features in the described preferred embodiments the abundance histogram is relative.

According to still further features in the described preferred embodiments the abundance histogram serves for the classification of the at least one cell into the cell class of step (d).

According to still further features in the described preferred embodiments the classification of each of the pixels into the classification groups according to the pixels spectra of step (c) is effected using a classification map algorithm which employs reference spectra for associating pixels into the classification groups.

According to still further features in the described preferred embodiments the reference spectra for classification are of a previously prepared reference library.

According to still further features in the described preferred embodiments at least one of the reference spectra for classification is of pixels derived from a cell domain selected from the group consisting of nucleolus, inter-chromosomal region, cytoplasm, a first chromatin region of the nucleus, a second chromatin region of the nucleus and background.

According to still further features in the described preferred embodiments pixels classified to a classification group via the classification map algorithm are presented in an image by a preselected artificial color.

According to still further features in the described preferred embodiments pixels classified to a classification group via the classification map algorithm are presented as an abundance histogram.

According to still further features in the described preferred embodiments the abundance histogram serves for the classification of the at least one cell into the cell class of step (d).

According to still further features in the described preferred embodiments the abundance histogram serves for the classification of the at least one cell into the cell class of step (d) via a trained neural network algorithm which associates abundance histogram s with cell classes.

According to still further features in the described preferred embodiments the classification of each of the pixels into the classification groups according to the pixels spectra of step (c) is effected using a first trained neural network algorithm which associates a pixel into a classification group according to the pixel's spectrum.

According to still further features in the described preferred embodiments pixels classified to a classification group via the first trained neural network algorithm are presented in an image by a preselected artificial color.

According to still further features in the described preferred embodiments pixels classified to a classification group via the first trained neural network algorithm are presented as an abundance histogram.

According to still further features in the described preferred embodiments the abundance histogram serves for the classification of the at least one cell into the cell class of step (d) via a second trained neural network algorithm which associates abundance histogram s with cell classes.

According to still further features in the described preferred embodiments the cell is a cancer cell, such as carcinoma, sarcoma, leukemia, lymphoma and the like.

The present invention successfully addresses the shortcomings of the presently known configurations by providing a method for automatic or semi automatic and therefore less subjective method for classification and grading of neoplasm. Furthermore, the method of the present invention provides spectrally resolved morphometric classification images which may be used by pathologists for classification and grading of neoplasm, which images replace the prior art RGB images and lead to a less subjective interpretation of the results and therefore, to a more accurate classification. This in turn may affect diagnosis, treatment and prognosis.

BRIEF DESCRIPTION OF THE DRAWINGS

The invention herein described by way of example only, with reference to the accompanying drawings, wherein:

The file of this patent contains at least one drawing executed in color photograph. Copies of this patent with color photograph(s) will be provided by the Patent and Trademark Office upon request and payment of necessary fee.

FIG. 6 shows six averaged reference spectra, each derived from a different cellular location, as exemplified in FIG. 5a, the reference spectra were employed to construct the classification maps of FIGS. 5a–h;

FIGS. 7a–h show total area histograms of the classification maps of nuclei of the cell types exemplified in FIGS. 5a–h, respectively;

FIGS. 8a–h show percent area histograms of the classification maps of nuclei of the cell types exemplified in FIGS. 5a–h, respectively;

FIGS. 9a–h show regions highlighted by the first principal component, derived from a principal component analysis of the cells of FIGS. 5a–h, respectively.

DESCRIPTION OF THE PREFERRED EMBODIMENTS

The present invention is of spectral bio-imaging methods which can be used for automatic and/or semiautomatic spectrally resolved morphometric classification (e.g., grading) of cells (e.g., neoplasm, embryonic cells, etc.). Specifically, the present invention can be used to detect cellular spatial organization and to quantify cellular and tissue constituents and structures associated with tumorogenesis using light transmission microscopy combined with high spatial and spectral resolutions. The methods can also be used for classification of cells into developmental stages, and to qualify and quantify metabolic processes within cells. The method can further be used to develop new and more fine tuned indexes for neoplasm classification.

SPECTRAL IMAGING SYSTEMS

For purposes of better understanding the present invention, as illustrated in FIGS. 4–15h of the drawings, reference is first made to the construction and operation of some spectral imaging systems (i.e., imaging spectrometers).

Figure 1:
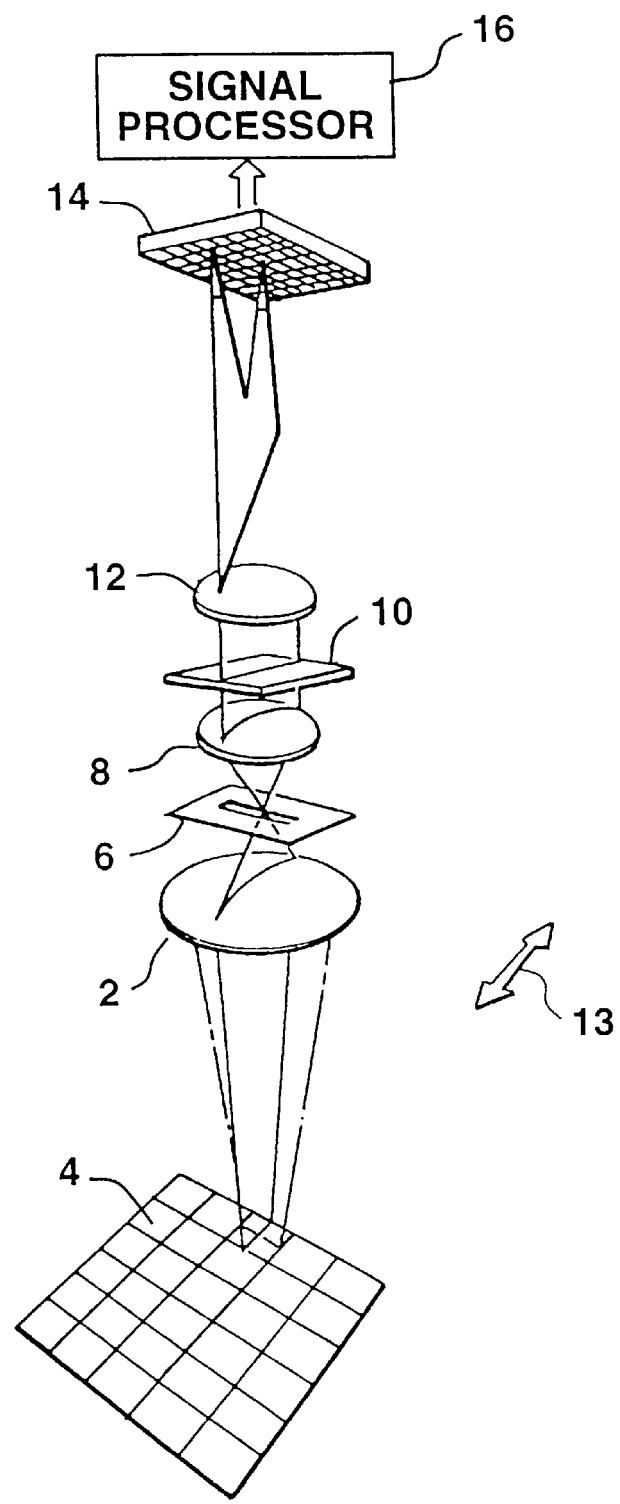
FIG. 1 illustrates a conventional (prior art) slit-type imaging spectrometer.

A conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system as indicated at 2, for collecting the incident light from a scene, schematically indicated at 4 and focusing the substantially parallel light of the scene 4 onto a first focal plane occupied by a slit 6 to define the field of view. The light exiting from slit 6 is collimated in a collimator lens 8 and is passed through a spectral dispersion element 10 (e.g., a grating or a prism) to separate the various wavelengths. The output from spectral dispersion element 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., a raster movement or line scanning indicated by arrow 13) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time. This is necessary to separate the spectra of each pixel.

As mentioned in the background section and hereinabove, the disadvantage of the prior art method illustrated in FIG. 1 is that most of the pixels of one frame are not measured at any given time even though the optical system 2 actually collects light energy from all of them simultaneously. As a result, the required frame time is significantly increased, and/or the signal-to-noise ratio (sensitivity) is substantially decreased with respect to a system which does not have the need for such a slit.

Figure 2:
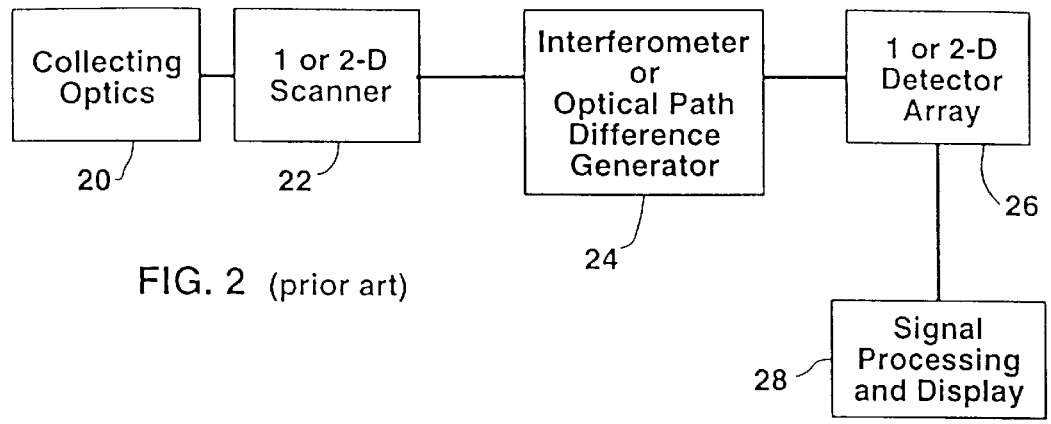
FIG. 2 is a block diagram illustrating the main components of an imaging spectrometer constructed in accordance with U.S. patent application Ser. No. 08/392,019 (prior art)

FIG. 2 is a block diagram illustrating the main components of an improved prior art imaging spectrometer disclosed in U.S. patent application Ser. No. 08/392,019 to Cabib et al., filed Feb. 21st, 1995, now U.S. Pat. No. 5,539,517, issued Jul. 23, 1996, which is incorporated by reference as if fully set forth herein. This imaging spectrometer is constructed highly suitable to implement the methods of the present invention.

Thus, the prior art imaging spectrometer of FIG. 2 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum of each pixel. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, few alternative types of interferometers may be employed. These include (i) a moving type interferometer in which the OPD is varied to modulate the light, namely, a Fabry-Perot interferometer with scanned thickness; (ii) a Michelson type interferometer which includes a beamsplitter receiving the beam from an optical collection system and a scanner, and splitting the beam into two paths; (iii) a Sagnac interferometer optionally combined with other optical means in which interferometer the OPD varies with the angle of incidence of the incoming radiation, and (iv) a four-mirror plus beamsplitter interferometer as further described and exemplified in the cited U.S. patent application.

Figure 3:
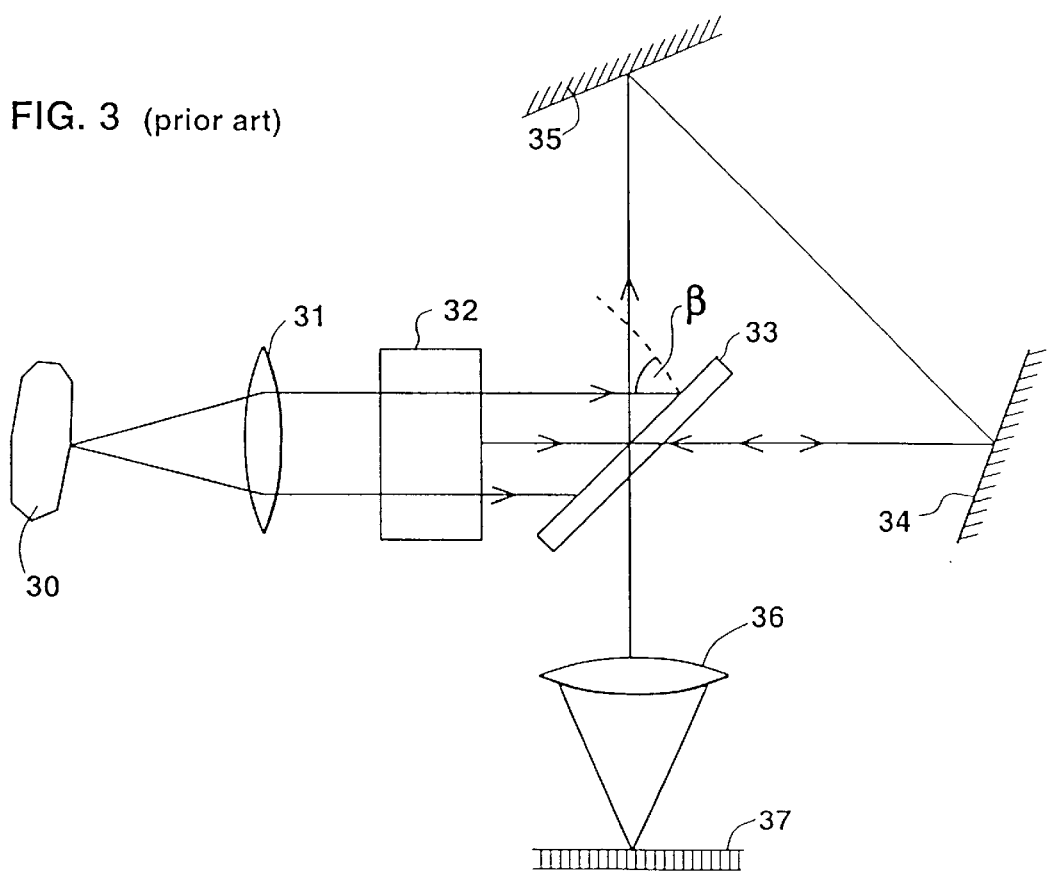
FIG. 3 illustrates a non-moving type interferometer, namely, a Sagnac interferometer, as used in an imaging spectrometer in accordance with U.S. patent application Ser. No. 08/392,019 (prior art)

FIG. 3 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies linearly with this angle.

In the interferometer of FIG. 3, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

To perform the OPD scan the whole interferometer is rotated, or it is optionally combined with other optical elements which are rotated; alternatively, in the case of Michelson or Fabry Perot the scan is performed by the translation of a mirror.

At the end of a single scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 3 the ray (parallel to the optical axis) which is incident on the beamsplitter at an angle $\beta$ ($\beta=45°$ in FIG. 3) goes through the interferometer with an OPD =0, whereas a ray which is incident at a general angle $\beta-\theta$ undergoes an OPD given by the following:

$$OPD(\beta,\theta,t,n)=t[(n^2-\sin^2(\beta+\theta))^{0.5}-(n^2-\sin^2(\beta-\theta))^{0.5}+2\sin\beta\sin\theta]$$

where $\theta$ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

An imaging spectrometer in accordance with the invention disclosed in U.S. Pat. No. 5,539,517 was developed by Applied Spectral Imaging (ASI) Ltd., Industrial Park, Migdal Haemek, Israel and is referred hereinbelow as SpectraCube™. The SpectraCube™ system optically connected to a variety of optical devices was used to implement the methods of the present invention. The SpectraCube™ system has the following characteristics, listed hereinbelow in Table 1:

TABLE 1

| Parameter | Performance |
| --- | --- |
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 15–25 sec |
| FFT processing time: | 20–180 sec, typical 60 sec |

The SpectraCube™ system easily attaches to any microscope or macro lens with, for example, C-mount or F-mount connectors, and can stand in any orientation during the measurement. The system may as well be connected to other magnification means and to various types of endoscopes and cameras. Therefore, spectral images of cells and tissues in various magnification and lighting strategies may be obtained.

The SpectraCube™ system has numerous utilities. For examples of the use of the SpectaCube™ system for various biological applications, the reader is referred to U.S. patent application Ser. No. 08/571,047, and to E. Schroeck et al. (1996) Multicolor spectral karyotyping of human chromosomes. Science, 273, 494–497; Garini et al. (1996) Spectral Karyotyping, Bioimaging 4, 65–72; Malik et al. (1996) Fourier transform multipixel spectroscopy and spectral imaging of protoporphyrin in single melanoma cells, Photochemistry and photobiology 63, 608–614; Malik et al. (1996) Fourier transform multipixel spectroscopy for quantitative cytology, Journal of Microscopy 182, 133–140; Garini et al. (1996) Spectral Bio-Imaging, Fluorescence imaging spectroscopy and microscopy, chapter 4, ed. X. F. Wang and B. Herman, Chemical Analysis Series, Vol. 137, John Wiley and Sons; Soenksen et al. (1996) Use of novel spectral bio-imaging system as an imaging oximeter in intact rat brain, SPIE Proceedings 2679; Liyanage et al. (1996) Multicolor spectral karyotyping of mouse chromosomes, Nature Genetics 14, 312–315; all are incorporated by reference as if filly set forth herein.

The prior art SpectraCube™ system is used herein to acquire spectral data of every pixel of cancer cells. However, any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) based spectral imagers can be used to acquire the required spectral data. Therefore, it is intended not to limit the scope of the present invention for use of any specific type of spectral imager.

DISPLAY AND ANALYSIS OF SPECTRAL IMAGES a. General

As mentioned above, a spectral image is a three dimensional array of data, $I(x,y,\lambda)$, that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set, i.e., a spectral cube.

One possible type of analysis of a spectral cube is to use spectral and spatial data separately, i.e., to apply spectral algorithms to the spectral data and two-dimensional image processing algorithms to the spatial data.

As an example for a spectral algorithm consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor. according to its classification as being most similar to one of the several reference spectra. Both, similarity and classification mapping may employ any of the four following Equations (2–5).

The reference spectrum can be one corresponding to a pixel in the same image, or from a library or from another image.

There are many similarity map functions known in the literature, four are given hereinbelow (Equations 2–5):

$$G^{(1)}_{x,y} = \frac{I^2_{max}}{40\left(\left(\frac{1}{n}\sum_\lambda (I_{xy}(\lambda)-R_\lambda)^2\right)^{\frac{1}{2}} + \frac{I_{max}}{40}\right)} \quad (2)$$

$$G^{(2)}_{x,y} = \frac{I^2_{max}}{20\left(\left(\frac{1}{n}\sum_\lambda (I_{xy}(\lambda)-R_\lambda)^2\right)^{\frac{1}{2}} + \frac{I_{max}}{20}\right)} \quad (3)$$

$$G^{(3)}_{x,y} = \frac{I^2_{max}}{40\left(\frac{R_{max}}{S_{max}}\left(\frac{1}{n}\sum_\lambda (I_{xy}(\lambda)-R_\lambda)^2\right)^{\frac{1}{2}} + \frac{I_{max}}{40}\right)} \quad (4)$$

$$G^{(4)}_{x,y} = \frac{I^2_{max}}{40\left(\frac{R_{max}}{T_{max}}\left(\frac{1}{n}(\langle I_{xy}(l)\rangle - R_l)^2\right)^{\frac{1}{2}} + \frac{I_{max}}{40}\right)} \quad (5)$$

where $I_{max}$ is the maximum intensity of the image, $G_{x,y}$ is the brightness with which a pixel (of coordinates x and y) is displayed on the screen, $I_{x,y}(\lambda)$ is its spectrum, $\langle I_{xy}(\lambda)\rangle$ is the average of $I_{xy}(\lambda)$ over the group of 3×3 neighboring pixels, $S_{max}$ is the peak intensity of $I_{xy(\lambda)}$, $T_{max}$ is the peak intensity of $\langle I_{xy}(\lambda)\rangle$, $R_\lambda$ is the reference spectrum with respect to which the similarity map is calculated, $R_{max}$ is the peak intensity of the reference spectrum $R_\lambda$ and n is the number of wavelengths of the measurement.

When similarity mapping is performed, it is clear that according to the above Equations 2–5, in all cases, the more a pixel spectrum is similar to the reference spectrum, the brighter it will be displayed on the screen.

On the other hand, when classification is performed, a calculation using the spectrum of each of the pixels of the image, one at a time, and of each of the few reference spectra, one at a time, is performed (preferably after normalization of all spectra to a 0–100% intensity range), and the analyzed pixel is given a preselected arbitrary color according to the reference spectra to which it is most similar using for example a minimal square error calculation, as well known in the art.

It is also possible to apply spectral image algorithms based on nonseparable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., $I(x,y,\lambda)$), is visualizing that data structure in a meaningful way. Unlike other types of 3D data such as topographic data, D(x,y,z), obtained for example by a confocal microscope, where each point represents, in general, the intensity at a different locations (x,y,z) in three-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x, y) = \int_{\lambda_2}^{\lambda_1} w(\lambda) \cdot I(x, y, \lambda) d\lambda \qquad (6)$$

In Equation 6, $w(\lambda)$ is a general weighting response function that provides maximum flexibility in computing a variety of gray scale images, all based on the integration of an appropriately weighted spectral image over some spectral range. For example, by evaluating Equation 6 with three different weighting functions $\{w_r(\lambda), w_g(\lambda), w_b(\lambda)\}$, corresponding to the tristimulus response functions for red (R), green (G) and blue (B), respectively, it is possible to display a conventional RGB color image. It is also possible to display meaningful non-conventional (pseudo) color images.

Figure 4:
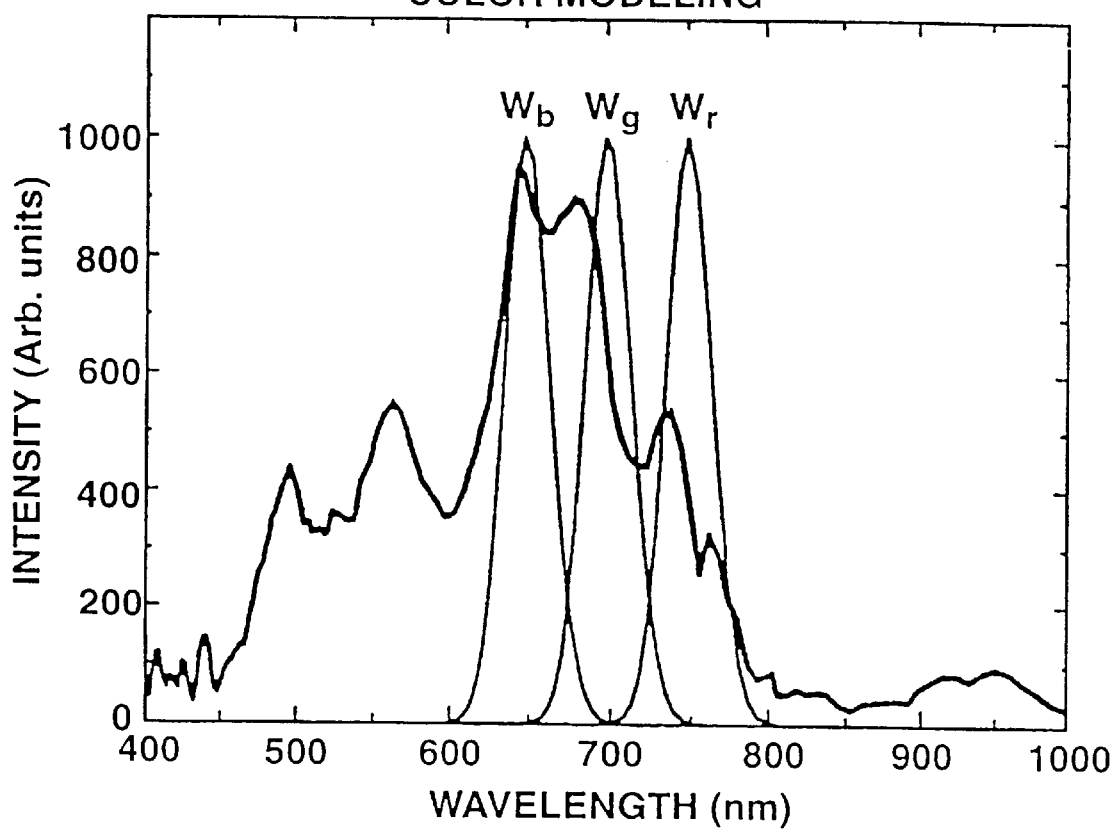
FIG. 4 shows a definition of pseudo-RGB (Red, Green and Blue) colors for emphasizing chosen spectral ranges. The intensity for each pseudo-color is calculated by integrating the area under the curve, after multiplying it by one of the curves.

FIG. 4 presents an example of the power of this simple algorithm. Consider choosing $\{w_r, w_g, w_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point Operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant.

The concept of point operations can also be extended to spectral images: here each pixel has its own intensity function (spectrum), i.e., an n-dimensional vector $V_1(\lambda)$; $\lambda \in [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \in [\lambda_1, \lambda_n] \qquad (7)$$

Building a gray scale image according to Equation 7 is an example of this type of point operation. In the more general case, a point operation maps the spectrum (vector) of each pixel into another vector according to a transformation function:

$$V_2(l) = g(V_1(\lambda)); l \in [1, N], \lambda \in [\lambda_1, \lambda_n] \qquad (8),$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10} \frac{I(\lambda)}{I_0(\lambda)} = -\log_{10} \tau(\lambda) \qquad (9)$$

where $OD(\lambda)$ is the optical density as a function of wavelength, $I(\lambda)$ is the measured spectrum, $I_0(\lambda)$ is a measured reference spectrum, and $\tau(\lambda)$ is the spectral transmitance of the sample. Equation 9 is calculated for every pixel for every wavelength where $I_0(\lambda)$ is selected from (i) a pixel in the same spectral cube for which OD is calculated; (ii) a corresponding pixel in a second cube; and (iii) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known.

Additional examples include various linear combination analyses, such as for example: (i) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (ii) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

c. Spatial-spectral Combined Operations

In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (i) classify each pixel in the image as belonging to one of k+1 classes (k cell types plus a background) according to its spectrum; (ii) segment the image into the various cell types and count the number of cells from each type; and (iii) sum the fluorescence energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. The ideal type of measurement for this type of situation is a spectral image. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; i=1, 2, ..., k, $\lambda \in [\lambda_1, \lambda_n]$, and the measured spectrum at each pixel (x, y) is $s_{x,y}(\lambda)$, $\lambda \in [\lambda_1, \lambda_n]$, then the following algorithm is a possible method of classification (step 1 above):

Let $e^2_i$ be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2 \qquad (10)$$

where $R_\lambda$ is the spectral region of interest. Each point [pixel (x, y)] in the image can then be classified into one of the k+1 classes using the following criterion:

point(x,y)∈class k+1 if $e^2_i$>threshold for all i∈[1,k], (11)

whereas point(x,y) ∈ class ρ if $e^2_i$<threshold, and ρ is such that min[$e^2_i$]=$e^2_\rho$ Steps ii and iii above (image segmentation and calculation of average fluorescence intensity) are now straightforward using standard computer vision operations on the synthetic image created in accordance with the algorithm described in Equations 10 and 11.

Another approach is to express the measured spectrum $s_{x,y}(\lambda)$ at each pixel as a linear combination of the k known fluorescence spectra $s_i(\lambda)$; i=1, 2, ..., k. In this case one would find the coefficient vector C=[$c_1, c_2, ..., c_k$] that solves:

$$F = \min \sum_{\lambda \in R_\lambda} (s(\lambda) - \hat{s}(\lambda))^2 \qquad (12)$$

where $\hat{s}(\lambda) = \sum_{i=1}^{k} c_i \cdot s_i(\lambda),$

Solving for $$\frac{dF}{dc_i} = 0;$$

for i=1, 2, ..., k(i.e., find values of $c_i$ which minimize F) yields the matrix Equation C=$A^{-1}$ B (13), where A is a square matrix of dimension k with elements $$a_{m,n} = \left[\sum_{\lambda \in R_\lambda} s_m(\lambda) \cdot s_n(\lambda)\right], \qquad (14)$$

and B is a vector defined as $$b_m = \left[\sum_{\lambda \in R_\lambda} s_m(\lambda) \cdot s(\lambda)\right], \quad m, n = 1, 2, ..., k. \qquad (15)$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes followup, spectral normalization, etc.

In many cases, objects (e.g., cancer cells) present in a spectral image differ from one another in chemical constituents and/or structure to some degree. Using a decorrelation statistical analysis such as principal component analysis by producing covariance or correlation matrices enhances these small differences.

Decorrelation statistical analysis is directed at extracting decorrelated data out of a greater amount of data, and average over the correlated portions thereof. There are a number of related statistical decorrelation methods. Examples include but not limited to principal component analysis (PCA), canonical variable analysis and singular value decomposition, etc., of these methods PCA is perhaps the more common one, and is used according to the present invention for decorrelation of spectral data. However, considering the fact that all decorrelation statistical methods including those listed above are related to one another, there is no intention to limit the scope of the invention to use of any specific decorrelation method. Specifically, there is no intention to limit the scope of the present invention to use of principal component analysis, as any other decorrelation statistical method may be alternatively employed. Information concerning the use and operation of the above listed decorrelation statistical methods is found in R. A. Johnson and D. W. Wichen, "Applied Multivariance Statistical Analysis, third edition, Prentice Hall (1992) and T. W. Anderson, An Introduction to Multivariance Statistical Analysis, second edition, Wiley and Sons (1984), both are incorporated by reference as if fully set forth herein.

Furthermore, as will become apparent from the descriptions to follow, the implementation of a decorrelation statistical method may be done using various modifications. As the concept of the present invention is not dependent upon any specific modification, it is the intention that the scope of the present invention will not be limited to any specific modification as described below.

Principal component analysis (PCA) is one of a number of powerful techniques used in multivariate statistical analysis. It is advantageous in cases where a large number of "results", which depend on a large number of possibly correlated variables forms the basic data set. Its strength lies in the fact that this data decomposition provides a transformation to decorrelated variables, while simultaneously averaging over correlated variables.

In this paragraph the PCA technique as applied to multispectral images of the same object is delineated. The basic data set, i.e., the spectral cube, is composed of k spectral slices of the same object, where each spectral slice is obtained at a different spectral band. Thus, the data set is composed of the spectra of all the pixels of the object. One of the objectives of looking at such a data set can be the characterization of the pixels into groups of similar spectra. Regard each spectral slice as a vector whose elements are the image pixels arranged into the column vector using a predetermined code. Call the spectral slices $X_m$, so that the term $x_{nm}$ signifies the n-th pixel of the m-th spectral slice. In such way, the matrix $x=\{x_{nm}\}$ carries the full information, so that each column is a spectral slice. Define a matrix y derived from matrix x by subtracting from each column, the column average. The various columns of the y matrix may be correlated, so that, some of the information carried by the data is correlated. The PCA technique decorrelates the information and reduces it only to decorrelated variables, so that the amount of "real" data pixels is smaller and easier to handle.

The correlations are obtained directly by computing the covariance matrix c defined by Equation 16:

$$c=y'y \quad (16)$$

where y' is the transpose of y. The i,j term of c is the covariance of the i-th slice with the j-th slice, i.e. if they are decorrelated this term vanishes. The diagonal of c is composed of the variances of each spectral slice. which can be regarded as a scale for the amount of information in this particular slice. Alternatively, this variance (its square root) can be regarded as the average contrast of this particular slice.

Linear algebra describes this situation as follows. The objects of interest (the pixels of the spectral slices, k of them) are points in a k dimensional space. The fact that the covariance matrix c shows correlations is represented by its having a rank smaller than k. This situation is called degeneracy and it means that the k (narrow band) spectral slices provide too much data relative to the information content. Reduction of the data is performed by finding the eigen system of the covariance matrix. Formally, this operation means that one has to find k vectors vm called eigenvectors and k scalars Am called eigenvalues so that (Equation 17):

$$c.v_m = \lambda_m v_m \quad (17)$$

for m=1, 2, . . . , k

In a case where the data is correlated, some of the eigenvalues vanish. The number of non-vanishing eigenvalues defines the dimension of the information, which dimension is smaller than k. The corresponding eigenvectors define a subspace in the original k space in which the full information content is represented. Furthermore, the information in each new dimension is completely decorrelated to the information in the other dimensions. Thus in the new space the full information content is represented in a decorrelated manner so that it can be easily used for classification purposes. For further details regarding the principal component analysis, the reader is referred to Martens and Naes (1989) Multivariate Calibration, John Wiley & Sons, Great Britain; and to Esbensen et al., Eds. (1994) Multi variance analysis—in practice; and, Computer-aided modeling as CAMO, and the Unscrambler's User's guide, Trondheim, Norway, both are incorporated by reference as if fully set forth herein.

It should be noted that such an analysis can be performed on a whole spectral cube. Preferably, the analysis is performed only for selected pixels or mathematically manipulated (e.g., after background subtraction and averaging) selected pixels to improve the results and enable better classification later on. The preferred approach is described in more detail below, nevertheless, there is no intention to limit the scope of the present invention to the preferred approach employed, as different mathematical manipulations may be found useful for different data collection approaches (e.g., filter or dispersion element based spectral imagers).

TRANSMISSION MICROSCOPY

Light microscopy is one of the most fundamental techniques for the visualization of cells and tissues in biology and pathology. Transmission microscopy suffers greatly from the inherently low contrast of cell organelles and structural details. Many methods have been developed to improve this contrast, among them staining and spatial filtering. The use of spectral bio-imaging methods of the present invention is one of the most straightforward methods to increase the apparent contrast of cells and tissues examined under a transmission microscope, thereby improving dramatically the identification and discrimination capabilities of this popular microscopic method. The basic approach proposed herein is to measure a spectral image, and to then use this large amount of information in conjunction with spectral and morphological analysis methods and algorithms in order to identify and map cellular and subcellular details.

In order to facilitate the histological examination of biological specimens, a variety of staining techniques were developed during the last century using organic stains which specifically bind to different macromolecules in the cells, though the molecular basis of the staining techniques has been and still is empirical. Other image contrast enhancement methods include the use of spatial filtering techniques such as dark field and polarization methods [see, Kam (1987) Quarterly Reviews of Biophysics, 20, pp. 201–259]. The most common staining techniques are the Romanowsky-Giemsa, Haematoxylin-Eosin mason tricolor and papanicolaou staining. The Romanowsky-Giemsa staining procedure uses a combination of two dyes, one of which is Azure-B (trimethyl methionine), a thiazin dye, and the second being Eosin Y (hydroxyxanthene bromide). The thiazines are cationic dyes and therefore bind to acidic cellular constituents, whereas Eosin is an anionic dye and tends to bind to basic cellular constituents. It is widely accepted that the use of these two components creates the so-called Romanowsky-Giemsa effect, which is expressed as the development of a specific purple color, a new dye complex, in some stained sites. The molecular basis of the azure-B-Eosin complex is obscure. Some authors think that azure-B binds to anionic structures such as the phosphate groups of DNA, and that Eosin simultaneously binds both with an adjacent cationic site on the DNA and with the azure-B. In a more recently proposed model of the azure-B-Eosin complex, Friedrich and colleagues [Friedrich et al. (1990) Histochemistry 93, pp. 247–256] have suggested that azure-B first binds to phosphodiester residues of the DNA molecule. The authors have hypothesized that the phenyl group of the Eosin molecule is the portion that binds to the azure-B molecule (which lies in a single plane). The color purple is a result of a red shift of the Eosin absorption peak, which in turn is caused by the dielectric polarization of bound Eosin. The very existence of such an azure-B-Eosin complex is still questioned by others [see, Friedrich et al. (1990) Histochemistry 93, pp. 247–256; Bottiroli et al. (1994) Lasers in Surgery and Medicine; Profio (1984) IEEE Journal of Quantum Electronics QE-20 pp. 1502–1506; Herman (1989) Fluorescence Microscopy of Living Cells in Culture, part B, Chapter 8, pp. 219–243, edited by Taylor and Wang, Academic Press Inc.; and, Jovin and Arndt-Jovin (1989) Cell structure and function by microspectrofluorometry, Chapter 5, Academic Press Inc.].

Whatever the technique, with staining it is possible to distinguish between subcellular compartments of the cell, and especially to distinguish the chromatin organization in the nucleus. It is well established that the ratio between heterochromatin, stained dark blue, and euchromatin, stained pink, is one of the major determinants in the evaluation of cells in tissue sections. Nevertheless, the results obtained from stained specimens remain, to some degree, a matter of experience, art, and subjective interpretation. In order to diminish the effect of the scientist's experience, there have been attempts to study the spectroscopic characteristics of the interaction between organic stains and macromolecules, and thus to evaluate the so-called Romanowsky-Giemsa Effect of DNA staining.

Spectral imaging applied to transmission light microscopy can greatly improve the quantitative measurement of size, shape and textural features of cell organs, cells and tissues. This technique is known as morphometry, which is a rapidly growing field in biology and pathology [Erler et al. (1993) Modern Pathology, 6, pp. 612–618]. Morphometric spectral image analysis enables the evaluation of subtle cytological and histological features to yield useful ultra-structural and medical information for diagnostic and prognostic evaluation [Hytiroglou et al. (1992) Cancer 69, pp. 88–212].

In some cases, spectral images acquired using transmission methods and unstained tissue may provide useful information, similar to that found in fluorescence microscopy techniques. One of the advantages of combining spectral bio-imaging and transmission microscopy is the ability to use a 'clean' measurement technique, i.e., no need for working with potentially toxic dyes or fixation agents.

Thus, according to the present invention there is provided a spectral bio-imaging method for cells (e.g., cancer cells) classification into classes. In a preferred embodiment of the invention the analyzed cell is a cancer cell, such as carcinoma, sarcoma, leukemia, lymphoma and the like. However, non-cancerous cells may also be analyzed to classify them into developmental and/or metabolic stages. These include embryonic cells and virus and/or bacteria infected cells.

It should be noted that when the term 'classification' is used herein with respect to cells, it refers to any type of categorization including but not limited to detection of cell types (e.g., cancerous or benign, type of cancer, etc.), cell developmental stage, cell grade (also know as stage), cell metabolic status, etc.

In a preferred embodiment of the invention the method includes the step of preparing a sample to be spectrally imaged. The sample preferably includes more than a single cell, yet the sample may include a single cell or even a portion of the cell such as the cell nucleus, as in many cases classification is based merely upon nucleus analysis (see Background section above). As is further described hereinbelow in Examples 1–3 of the Examples section, spectral data derived from the nucleus alone can serve for cell classification into classes. Preparing a sample to be spectrally viewed may involve thawing the sample (if previously frozen), slicing the sample into slices of suitable thickness (e.g., about 4 $\mu$m), mounting the slices onto a microscope slide, fixating the sample onto the slide and staining the sample. Additional preparation steps may be required depending on the specific application. Thus, for example, if the cells are of a non-solid tumor (e.g., cancerous blood cells), as a part of the preparation, such cells may be spread on the slide etc. Nevertheless, one of ordinary skills in the art could devise the required preparation steps for any specific application. In most cases it is desirable to stain the cells prior to analysis to increase the availability of spectral information therein. Different stains bind different cellular constituents in different affinities, yet due to the presence of stain, a spectrum which is unique to each stained constituent is obtained. Suitable stains include but are not limited to Haematoxylin-Eosin staining and Giemsa staining or for some applications immunostaining [see, for example, Goto M, Nagatomo Y, Hasui K, Yamanaka H Murashima S and Sato E (1992) Chromaticity analysis of immunostained tumor specimens. Pathol. Res. Pract. 188:433]. However, it will be appreciated that for some applications cells which have not been stained are also suitable or preferred. This depends in part on lighting strategy and type of microscope employed, all as well known in the art.

The method according to the present invention further includes the step of viewing the sample through an optical device which is optically connected to an imaging spectrometer. The optical device and the imaging spectrometer are used for obtaining a spectrum of each pixel of the sample. In a preferred embodiment of the invention the optical device is a microscope, such as a light transmitting microscope. Nevertheless, other types of microscopes such as but not limited to a phase contrast microscope, dark field microscope, fluorescent microscope and even a confocal microscope may be employed, provided that suitable staining (if so required and/or desired) and lighting strategies are employed. In yet another preferred embodiment of the invention the imaging spectrometer includes a dispersion element, a filter or an interferometer, to effect the collection of spectral information from each pixel viewed in the sample. Further detail concerning the operation of spectrometers including such elements are disclosed hereinabove. In a preferred embodiment of the invention the obtainment of the spectrum of each pixel is effected by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) scanning (e.g., rotating or translating) one or more of the elements of the interferometer system (e.g., the interferometer as a whole), so that the optical path difference between the two coherent beams generated by the interferometer system is scanned simultaneously for all the pixels of the sample; and (v) recording signals of each of the detector elements as function of time using a recording device to form a spectral cube of data. This scheme for obtaining the spectrum of each pixel is further detailed with respect to FIGS. 2 and 3, above.

The method according to the present invention further includes the step of classifying each of the pixels into classification groups according to the pixel's spectra. The number of classification groups is at least two. When the term 'classification' is used herein and in the claims with respect to pixels classification, it refers to any approach wherein a pixel is classified to a group according to its spectrum. In a case where only two classification groups are employed one group may include pixels belonging to that group, whereas the other may include pixels not belonging to the first group. In most cases however, more than two groups are of choice. In the Examples section below pixels of cell samples were associated with six groups (Examples 1–3) or seven groups (Example 4). In the later case one of the groups included unclassified pixels. In order to perform pixels classification, the spectra of the pixels are preferably first normalized to exclude variable intensity effects which may be attributed to irregularities associated with the examined sample (e.g., non homogenous thickness and/or staining) or with the measurement optics (the microscope and/or the imaging spectrometer). In a preferred embodiment of the invention, pixels classified to a classification group are presented in an image by a preselected artificial color. Preferably, each group is attributed a different color (see FIGS. 5a–h and 14a–h and associated descriptions in the Examples section below). Such color representations are in fact spectrally resolved morphometric images of the analyzed cells. These spectrally resolved morphometric images may be viewed by a skilled pathologist to enable less subjective pathological examination since, when properly classified, each color represents a cellular domain, such that changes in such domains associated with different classes (e.g., types, grades, stages, etc.) of neoplasm may be observed, identified, qualified and qualified much more readily than before. Nevertheless, a more quantitative way of presenting pixels classified to classification groups is via an abundance histogram which presents the total or preferably the relative number of pixels classified to each classification group, as shown in FIGS. 7a–h, 8a–h and 15a–h, and further detailed in the Examples section below.

The method according to the present invention further includes the step of analyzing the classification groups and thereby classifying the examined cell into a cell class (e.g., types, grades, stages, etc.). As mentioned above, classifying an examined cell into a cell class may be effected by viewing an image of the classified pixels, wherein pixels belonging to any of the classification groups are attributed a different artificial color. However, in a preferred embodiment of the invention the abundance histogram for any examined cell serves for the classification of the cell into its class. Yet, it will be appreciated that other quantitative schemes may be used for such classification of cells into classes. For example, any quantitative analysis of the spatial distribution of pixels belonging to one or more classification groups may serve for such classification of cell classes. Such an analysis may include, for example, the shapes or outlines associated with any one or more of the classification groups. This analysis is of course based on previous findings correlating between various structures of cellular domains and classes of various tumors, as further detailed in the Background section above. Nevertheless, using the spectrally resolved morphometric data according to the present invention will facilitate such analyses, since the cellular domains are much better recognized and defined, as they are spectrally recognized and presented in contrasting artificial colors, as opposed to their prior art recognition—an RGB image which is perceived by the eye or a video camera and which is devoid of most of the spectral information collected using the method of the present invention for cell classification. Furthermore, in such an RGB image, the different cellular segments which are differently colored in, preferably, contrasting artificial colors, are much less distinguishable.

In a preferred embodiment of the invention the classification of each of the pixels into the classification groups according to the pixel's spectra is effected using a classification map algorithm which employs reference spectra for associating pixels into the classification groups. Further detail concerning classification map algorithms are found hereinabove. In general, classification map algorithms are capable of associating measured spectra into classification groups by comparing each of the measured spectra to a set of reference spectra (which form a classification library), evaluating (e.g., calculating) the differences between each of the measured spectra and each of the reference spectra, and associating each measured spectra to a single reference spectra to which it has the highest resemblance (minimal difference). A difference threshold may be employed such that above it a spectrum will be classified as "not classified". In most applications the reference spectra for classification are of a previously prepared reference library. This is the case in Examples 1–3 below, wherein each reference spectrum employed is the average of few normalized spectra derived from equivalent cell domains of few cells. In a preferred embodiment of the invention, at least one of the reference spectra for classification is of pixels derived from a cell domain selected from the group consisting of nucleolus, interchromosomal region, cytoplasm, a first chromatin region of the nucleus, a second chromatin region of the nucleus and background.

In one embodiment the pixels which where classified to a classification group via the classification map algorithm are presented in an image by a preselected artificial color, essentially as hereinabove described. In another preferred embodiment of the invention, the pixels classified to a classification group via the classification map algorithm are presented as an abundance histogram . Preferably, the abundance histogram serves for the classification of the examined cell(s) into the cell class(es), by for example viewing the histogram(s) and evaluating the occupancy of pixels classified to one or more classification group(s). More preferably, the abundance histogram of an examined cell serves for the classification of the cell into the cell class via a trained neural network algorithm which associates abundance histogram s with cell classes. An example for this type of classification is given under Example 4, below.

In another preferred embodiment of the invention the classification of each of the pixels into the classification groups according to the pixels spectra is effected using a first trained neural network algorithm which associates a pixel into a classification group according to the pixel's spectrum. In a preferred embodiment, pixels classified to a classification group via the first trained neural network algorithm are presented in an image by a preselected artificial color. In another preferred embodiment, pixels classified to a classification group via the first trained neural network algorithm are presented as an abundance histogram, which preferably serves for the classification of the examined cell into the cell class via a second trained neural network algorithm which associates abundance histogram s with cell classes. Further detail concerning the neural network algorithms, accompanied by specific examples are given hereinbelow under Example 4.

Reference in now made to the following examples, which together with the above descriptions, illustrate the invention.

EXAMPLE 1

Materials and methods:

Samples: Twenty one tumors—15 of infiltrating duct carcinoma, histological grade II and 6 of infiltrating lobular carcinoma, were selected from the surgical pathology material of the Sheba Medical Center, Department of Pathology. The material consisted of lumpectomy and mastectomy specimens stored in phosphate-buffered formalin.

Histology: Formalin-fixed paraffin-embedded tissues were cut into 4 micron thick sections, and stained with Haematoxylin-Eosin. All sections were reviewed by two independent pathologists and diagnosis was made by the criteria described by the WHO [Hartmann W H, Ozzello L, Sobin L H, Stalsberg H (1981). Histologic typing of breast tumors, eds. 2 Geneva: World Health Organization, 1–29; and Scarff R W, Torloni H (1968). Histologic typing of breast tumors. International Classification of tumors, vol. 2. Geneva: World Health Organization 19–20, which is incorporated by reference as if fully set forth herein]. The histological grading was made by the system of Bloom and Richardson, which considers tubular formation, nuclear pleomorphism and frequency of mitoses [Gallager H S, Hutter R V P (1978). Pathology and pathogenesis of breast cancer. In: Gallager H S, Leis H P, Snydcran R K. Urban I A. eds. The Breast. St Louis: C V Mosby 49–60]. All cases were searched for foci of in situ carcinoma. Nine out of the 15 cases of infiltrating duct carcinoma and 3 out of the 6 cases of infiltrating lobular carcinoma were associated with an in situ component. For comparison, 3 cases of areas representing normal breast epithelium were evaluated.

Fourier-Transform Multipixel Spectrometry System for Microscopy: The SpectraCube™ system (Applied Spectral Imaging (ASI) ltd., Industrial Park, Migdal Haemek, Israel) was used for spectral imaging of the samples. The SpectraCube™ system employed includes a Sagnac interferometer which is a particular type of triangular interferometer (see FIG. 3 above) and has high mechanical and thermal stability. The light beam passing through the specimen is split in the interferometer in different directions, and is united again at the exit with an optical path difference (OPD) which is a function of the angle ($\theta$) between the incoming beam and the optical axis of the interferometer itself. The OPD arises because for non-zero angles the two beams undergo different optical paths in the beamsplitter. The inherent mechanical stability of this interferometer allows the Fourier technique to be successfully applied to the visible spectral region. Wavelength calibration is performed by measuring a series of known monochromatic sources and then building a quadratic best-fit table of the wavelength versus "channel" parameter, the independent variable proportional to $1/\lambda$ (resulting from the fast Fourier transform, FFT). The interferometer forms interference fringes at infinity, so that they show up on the CCD focal plane as lines of intensity modulation superimposed on the image of the sample. The actual measurement is done by recording successive CCD frames in synchronization with the steps of the motor used to rotate the collimated beam, so that the instantaneous OPD is known for every pixel in every recorded frame and can be used in the FFT calculation. During a measurement, each pixel of the CCD (512×512, in this case) is collecting the interferogram, which is then Fourier transformed to give the spectrum thereof. The spectral and spatial resolutions, spectral range and other characteristics of the system employed are summarized in Table 1, above.

Spectral classification analysis: For spectral analysis of the breast carcinoma cells 6 different spectral regions were employed. These included the nucleolus, two distinct chromatin regions of the nucleus, an inter-chromosomal region, the cytoplasm and a low density space. The average spectra of each region sampled from 15 different cells was used to construct a spectral reference library for spectral classification analysis. To this end, the spectral reference library was served to scan all cells, assigning an arbitrary (pseudo, artificial) color to each spectrally similar region. For further detail concerning spectral classification, see above.

EXAMPLE 2

Spectral imaging was used to measure the light intensity at any wavelength over >$10^4$ pixels of the different cellular compartments of breast carcinoma cells stained with Haematoxylin-Eosin.

Figure 5A:
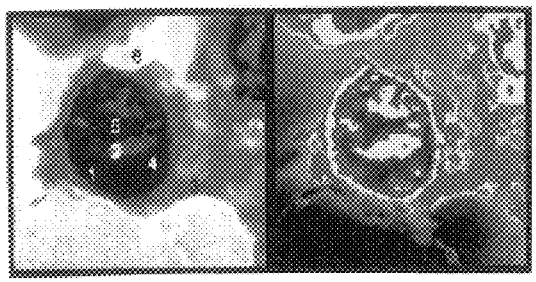
FIGS. 5a–c show three in situ ductal carcinoma cells stained with Haematoxylin-Eosin derived from three different patients of the types known in the art as in situ-duct-solid (FIG. 5a), in situ-duct-cribriform (FIG. 5b) and in situ-duct-comedo (FIG. 5c), right—RGB images; left—classification maps using the reference spectra of FIG. 6.

With reference to FIGS. 5a and 6. To this end, a spectral library was constructed of 6 separate spectral groups (assigned the numbers 1–6 in FIG. 5a) representing different domains of cells: nucleolus (marked as 1), two distinct chromatin regions of the nucleus (marked as 4 and 5), an inter-chromosomal region (marked as 2), cytoplasm (marked as 3) and a low density space or background (marked as 6). Each spectral group is an average of 15 spectra sampled from different cells and is represented in FIG. 6 by a different arbitrary color and its associated reference number (1–6).

Figure 5E:
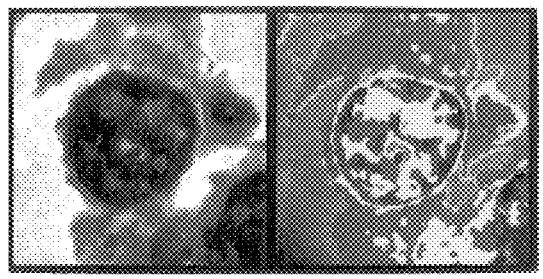
FIGS. 5e–f show three infiltrating (i.e., invasive) ductal carcinoma cells stained with Haematoxylin-Eosin of the types known in the art as infiltrating-duct-solid (FIG. 5e), infiltrating-duct-cribriform (FIG. 5f) and infiltrating-duct-comedo (FIG. 5g), these cells were derived from the same patients from which the cells presented in FIGS. 5a–c, respectively, were derived; right—RGB images; left—classification maps using the reference spectra of FIG. 6.
Figure 5B:
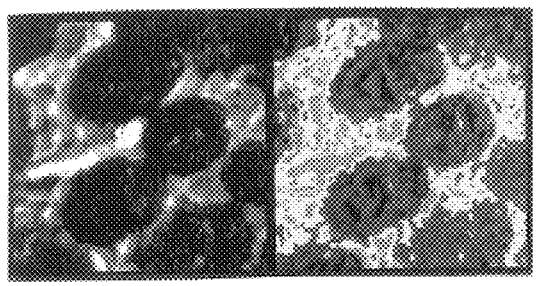
Figure 5F:
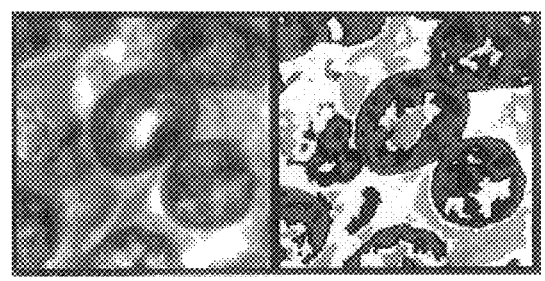
Figure 5C:
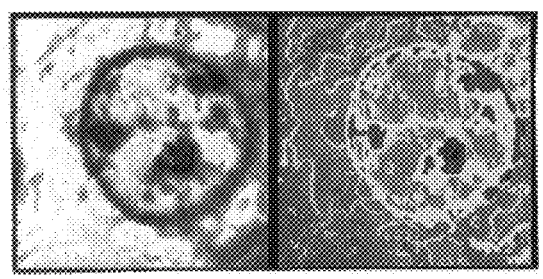

FIGS. 5a–c show three in situ (i.e., non invasive) ductal carcinoma cells derived from three patients stained with haematoxylin-Eosin of the types known in the art as in situ-duct-solid (FIG. 5b), in situ-duct-cribriform (FIG. 5b) and in situ-duct-comedo (FIG. 5c).

Figure 5G:
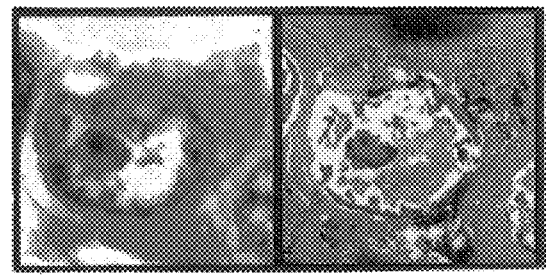
FIG. 5d shows an in situ lobular carcinoma cell stained with Haematoxylin-Eosin, derived from a fourth patient; right—an RGB image; left—a classification map using the reference spectra of FIG. 6.
FIG. 5h shows an infiltrating lobular carcinoma cell stained with Haematoxylin-Eosin, these cells were derived from the same patient from which the cells presented in FIG. 5d were derived; right—an RGB image; left—a classification map using the reference spectra of FIG. 6.

FIGS. 5e–g show three infiltrating (i.e., invasive) ductal carcinoma cells stained with Haematoxylin-Eosin of the types known in the art as infiltrating-duct-solid (FIG. 5e), infiltrating-duct-cribriform (FIG. 5f) and infiltrating-duct-comedo (FIG. 5g), derived from the same three patients, respectively.

Figure 5D:

FIG. 5d shows an in situ lobular carcinoma cell stained with Haematoxylin-Eosin, derived from a fourth patient.

Figure 5H:
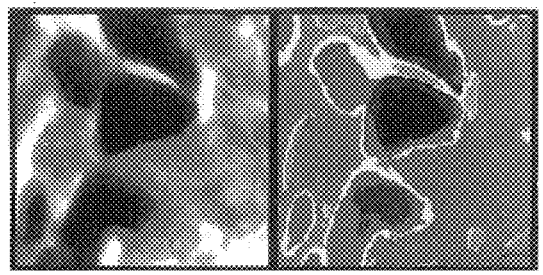

Whereas, FIG. 5h shows an infiltrating lobular carcinoma cell stained with Haematoxylin-Eosin, derived from the fourth patient.

For each of the cells shown in FIGS. 5a–h, an RGB image calculated from the spectral cube information, as described above, is shown on the left. As is apparent from the RGB images of FIGS. 5a–c and 5e–g, chromatin domains in the nuclei of these cells are demarcated by stain-chromatin complexes, seen as dense-color sites. Please note that the Haematoxylin-Eosin stained cells of FIGS. 5a–c and 5e–g show differences in nuclear size, structure and chromatin condensation.

For each of the cells shown in FIGS. 5a–h, a classification map, in accordance with the method of the present invention, is shown on the right. In these maps, each pixel in the image is attributed an artificial (pseudo) color selected from six different colors (red, yellow, green, purple, black and orange), according to the similarity of its spectrum to one of the reference spectra 1–6 shown in FIG. 6, respectively. Classification was performed using normalized spectra (both experimental and reference) in order to eliminate intensity variations.

Table 2 summarizes the relations among the 1–6 reference spectra, the artificial color attributed to pixels having spectra which is most similar to any of the 6 reference spectra, and the cellular origin of each of the reference spectra used for classification.

TABLE 2

| Number | Color | Cellular domain |
|---|---|---|
| 1 | red | nucleolus |
| 2 | yellow | inter-chromosomal region |
| 3 | green | cytoplasm |
| 4 | purple | a first chromatin region of the nucleus |
| 5 | black | a second chromatin region of the nucleus |
| 6 | orange | background |

As apparent from the classification maps shown in FIGS. 5a–h, distinct spectral regions of each of the cellular domains are differently colored, such that each colored region corresponds to one of the 6 domains. Thus, the reconstructed classification maps represent regional spectral similarities with respect to the reference spectra of FIG. 6.

With reference now to FIGS. 7a–h and 8 a–h. As was determined by the classification map algorithm, the area covered by (i.e., occupation) each of the six classified spectral regions which appeared in the nucleus of each of the cells exemplified in FIGS. 5a–h and thirteen additional cells of a known histological classification was determined, and the averaged areas categorized by numbers from 1–6 in accordance with the numerical references of the reference spectra shown in FIG. 6 and listed in Table 2 are presented histographically in the abundance histogram s in FIGS. 7a–h (total area) and 8a–h (relative area in percents) for each of the cell types, respectively. Table 3 summarizes the data of FIGS. 8a–h.

TABLE 3

| reference spectra | 1 | 2 | 3 | 4 | 5 | 6 |
|---|---|---|---|---|---|---|
| in situ-duct-solid | 12.22 | 29.68 | 1.13 | 33.17 | 5.67 | 5.76 |
| in situ-duct-cribriform | 0.00 | 9.53 | 0.00 | 17.23 | 9.90 | 0.00 |
| in situ-duct-comedo | 16.85 | 46.91 | 9.46 | 1.12 | 0.19 | 19.19 |
| in situ-lobular | 2.68 | 0.00 | 0.00 | 7.58 | 14.33 | 0.00 |
| infiltrating-duct-solid | 11.78 | 21.29 | 0.54 | 31.42 | 4.80 | 4.80 |
| infiltrating-duct-cribriform | 0.00 | 7.44 | 0.00 | 15.39 | 11.36 | 2.48 |
| infiltrating-duct-comedo | 24.44 | 38.01 | 11.42 | 0.94 | 0.00 | 17.98 |
| infiltrating-lobular | 10.40 | 0.00 | 0.00 | 29.40 | 55.60 | 0.00 |

Few conclusions can be drawn from the above results.

First, comparing between nuclear regions of in situ and the infiltrating cells, of all histological categories, reveals broad resemblance of the spectral elements and their relative occupation in the nucleus.

Second, the nuclear regions of the in situ solid, cribriform and comedo cells display differing occupations of spectral regional identities. This observation is statistically significant as cells from different patients displayed distinct spectral characteristics. For example, as shown in FIG. 8a–c, and 8e–g, nuclear regions 4 and 5 are more abundant in duct-solid and duct-cribriform then in duct-comedo tumors, regardless of their invasiveness, whereas nuclear region 3 is more abundant in duct-comedo tumors then in duct-solid and duct-cribriform tumors, regardless of their invasiveness, indicating that duct-solid and duct-cribriform tumor cells are of a more similar origin.

Third, in situ and infiltrating lobular carcinoma cells exhibited almost identical similarity maps for cells of in situ and infiltrating sites from different patients (FIGS. 5d and 5h and 8d and 8h). For each patient the in situ and infiltrating cells yielded similar classification maps. This similarity extended to the whole group of examined patients.

Thus, the averaged spectral arrays are significantly different for lobular and ductal carcinomas, and within the group of infiltrating duct carcinoma. However, the differences between distinct cases of infiltrating lobular carcinoma are statistically insignificant. No significant difference is observed between intraduct and infiltrating ductal lesions from the same patient or between lobular in situ and infiltrating lesions from all patients evaluated. By evaluation of the Figures representing the lobular carcinoma, a pattern consisting with unique spectral parameters of the infiltrating and in situ lobular cells can be constructed. The spectra labeled as 1, 4 and 5 in the spectral library of FIG. 6 seem to be highly related to the lobular carcinoma cells.

EXAMPLE 3

Another independent method used for evaluation of the cells was the principal component analysis (PCA). Light transmittance through Haematoxylin-Eosin stained cells is largely dependent on the oxidized hematoxylin (the purple hematein dye), which forms a complex with the nuclear chromatin. In order to demarcate light transmittance regions in the nucleus, the mathematical procedure of principal component analysis (PCA) was applied. PCA enhances the information content and arranges the information in a new series of images.

According to the PCA analysis few principal components are used to provide gray level nuclei images presenting different content of any specific principal component. In FIGS. 9a–h the distribution of the first component in the cells of FIGS. 5a–h, respectively, is presented. In other words, each of the pixels in the images of FIGS. 9a–h is attributed a darker shade, should it include more of the first component, and vice versa. As a result, two main nuclear domains were revealed, one having low intensity light transmittance (LIT) and the other having high intensity light transmittance (HIT). The first principal component highlighted the HIT (high intensity transmitance) regions of nuclear components, whereas LIT regions of chromatin were highlighted by the second principal component (not shown).

Figure 10A:
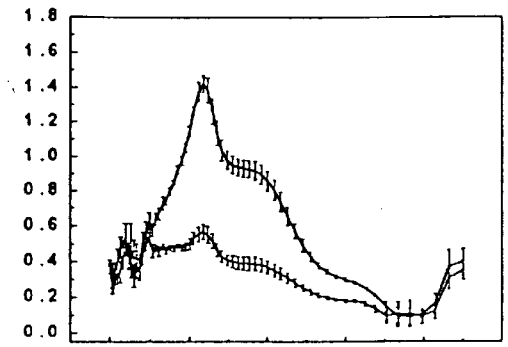
FIGS. 10a–h show optical density plots each is the average of 10 random pixels derived from regions highlighted by the first principal component, which are the dark regions in FIGS. 9a–h, and 10 random pixels derived from regions highlighted by the second principal component which are the light regions in FIGS. 9a–h.
Figure 10B:
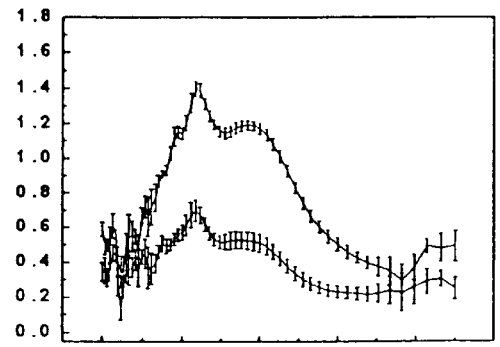
Figure 10C:
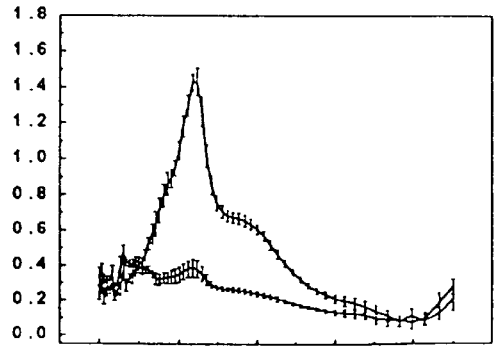
Figure 10D:
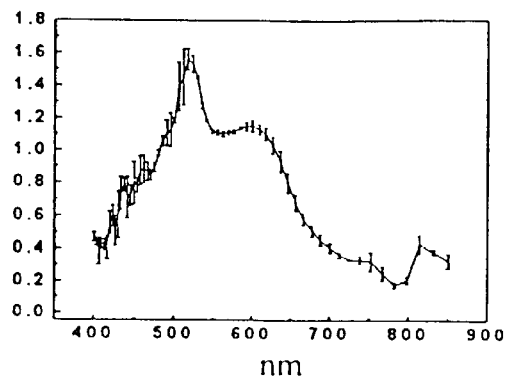
Figure 10E:
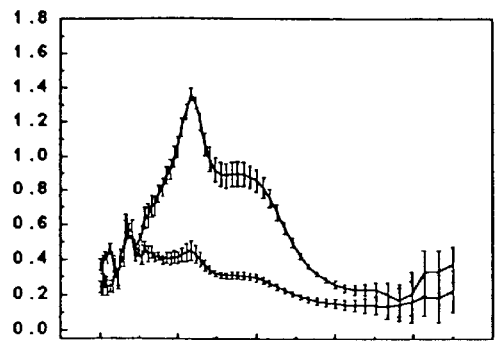
Figure 10F:
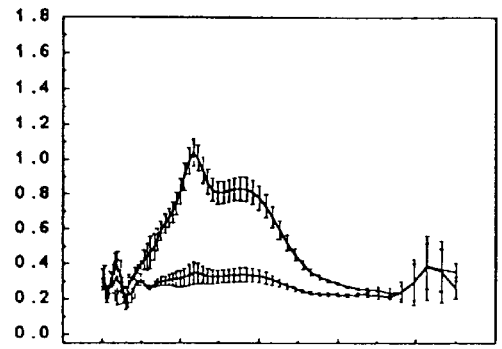
Figure 10G:
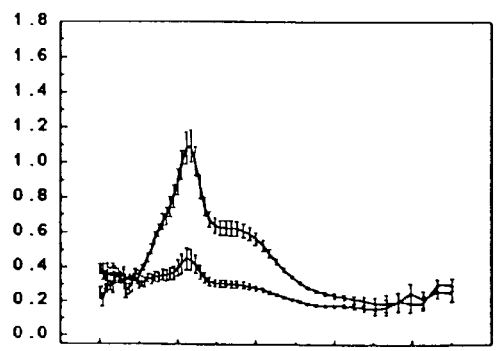
Figure 10H:
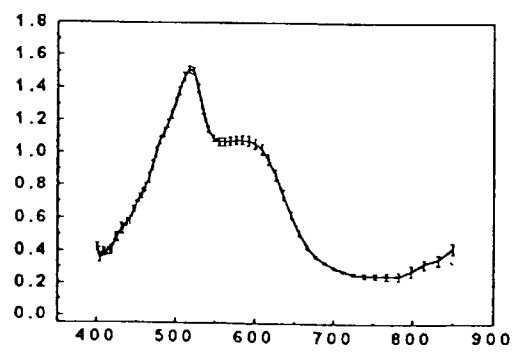

Using the demarcated borders depicted by the images, 10 pixel-spectra of is HIT and LIT domains were arbitrarily chosen. The average optical density displays of these spectra are presented in FIGS. 10 a–h. In all cases LIT is represented by the plot of higher optical density. In FIGS. 10d and 10h only optical density of pixels derived from LIT domains are displayed.

Strikingly, the optical density plots of FIGS. 10a–h, reveal similar similarities and dissimilarities among the examined cells, which similarities and dissimilarities were previously described with respect to the analysis of the classification maps of these cells. For example, note the location and shape of the shoulders in the LIT plots in the Figure pairs 6a–6e; 6b–6f; 6c–6g; and 6d–6h.

EXAMPLE 4

Another approach undertaken for classification of pixels into groups according to their spectra and for classification of cells into classes employed neural network algorithms.

Neural network computation is based on the concept of performing complicated computations by using many single elements operating in parallel. The concept of the "simple" computational element, called a neuron, was inspired by the biological nervous system, hence the name "neural network".

The computational neuron can be described as including two stages, the summing stage and a non-linear function stage. The input to a neuron includes n numbers, which are regarded as an n-vector p, wherein p=[$p_1$, $p_2$...$p_n$]. A neuron excited by this n-vector, produces a number composed of the weighted sum S of the input vector, mainly:

$$S = \sum_{k=1}^{n} W_{1k} * p_k \quad (18)$$

or in matrix notation S=W*p. Matrix W, which is called the neuron coupling weights, is a specific property of the neuron.

Figure 11:
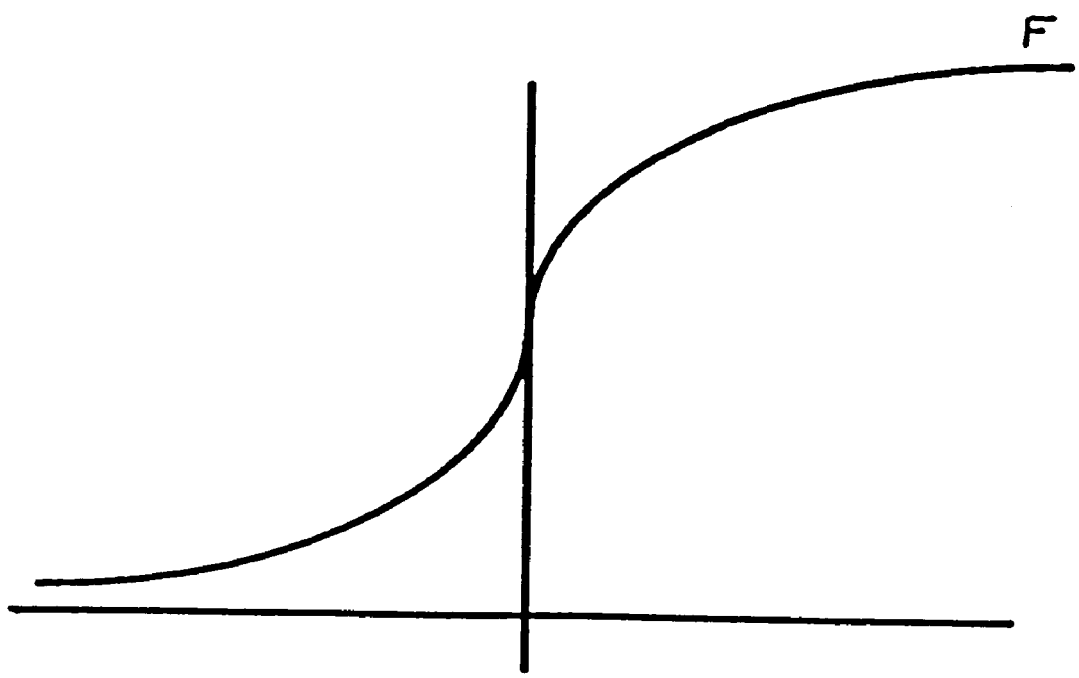
FIG. 11 shows a general outline of a non-linear F clipping function.

To this number, a second neuron specific number called the neuron bias is added, namely S1=S+b. This result is fed as an input to a non-linear function F. The output is the neuron output called t. Consequently, one can describe the neuron operation on the input vector, p, as t=F(W*p+b). Function F usually is a clipping function, i.e. it divides the continuous input into two categories, usually 0 and 1. Graphically, this function can be described essentially as shown in FIG. 11.

A neural network includes a layer of, say, m neurons, each with its specific weights and biases, operating in parallel on the input vector p. As such, a neural network produces m outputs regarded as an m-vector called t. Thus, the neural network which includes a layer of m neurons couples or associates the n-space of input vectors, to the m space of output vectors. The connection between the two spaces is dictated by the neurons weights and biases. A network can be made more complex by adding additional layers of neurons. The second layer is fed by the first layer output (the m-vectors t) producing the second layer output, and so on. Adding the additional layers adds more degrees of freedom to the system (coupling weights and biases) thus enables to produce more complex relations between the input and output.

An existing network, depending on its complexity and parameters, couples or associates a region of the input space to a region of the output space. Consequently, an input belonging to the proper region of the input space will, by transferring it through the network, be assigned to or associated with a specific region of the output space. In other words, the network can classify the input. The class it belongs to, is read in the output space. A network can be taught to perform specific classification tasks. This learning or training process is essentially the determination of the coupling weights and biases of each neuron in the network. One of the most effective learning or training technique is called backpropagation.

In principle, the back propagation method is based on the construction of a learning set and its use to determine the neurons parameters. In this method, the network size and complexity (number of neurons in each layer and number of layers in the network) is determined by the operator skill and not by a rigorous mathematical algorithm.

The training set includes a set of input vectors and a set of output vectors. The input vectors are representatives of the various classes in the input space and are determined or chosen by the operator. The output vectors correspond to the input vectors and describe the class each of which belongs to. The exact formulation of an output class is decided upon by the operator.

After the network architecture is selected, the coupling weights and biases of each neuron are chosen randomly. The input vectors in the training set are transferred through the network and the Euclidean distance between the input vectors and the corresponding output vectors in the training set are calculated. The variable consists the sum of the squared distances, the sum being over all vectors in the training set and is a function of all the neuron parameters. Using known numerical iterative techniques, a minima for this variable is found. The neurons parameters thus found determine the network parameters for the given task. An input vector belonging to a given region of the input space, is assigned to its proper position in the output space by transferring it through the neural network.

Further detail concerning neural networks and the back-propagation training technique are found in numerous text books and papers, including R. P. Lippman (April, 1987) An introduction to computing with neural nets. IEEE ASSP magazine pp. 4–27; T. P. Vogl, J. K. Mangis, A. K. Rigler, W. T. Zink and D. L. Alkon (1988) Accelerating the convergence of the backpropagation method. Biological cybernetics 59:257–263; D. E. Rumelhart, G. E. Hinton and R. J. Williams "Learning internal representations by error propagation" In Parallel Data Processing Vol. 1, Cha. 8 pp. 318–362, MIT press, Cambridge, Mass., USA, 1986: all are incorporated by reference as if fully set forth herein. A suitable network software include Neural-UNSC, software for multivariate calibration applying artificial neural network, version 1.02 (1993) CAMO A/S Olav Tryggvasonat 24, N-7011 Trondheim, Norway, the manual guide of which is incorporated by reference as if fully set forth herein.

Classification using a neural network algorithm as hereinbelow described employed the same spectral cubes used for the analysis described under Example 2.

Figure 12:
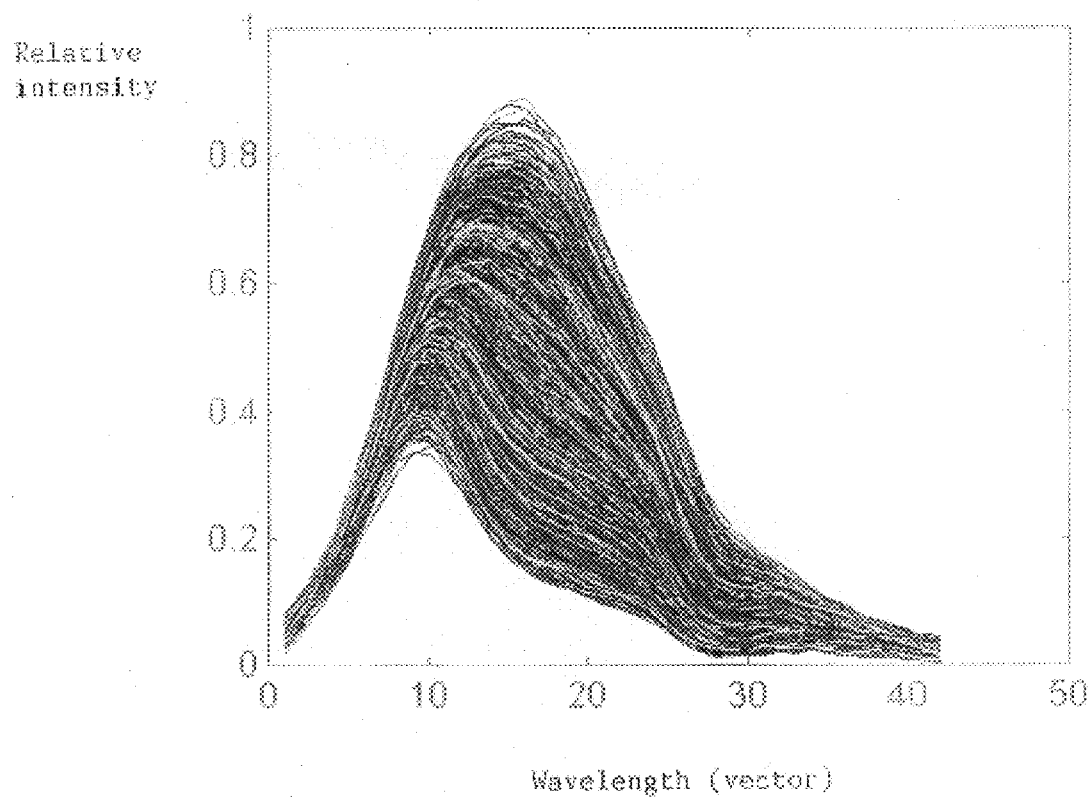
FIG. 12 show the profile of all pixel's spectra over an image of infiltrating-duct-cribriform tumor shown in FIG. 5f. Each spectrum is represented as a 42-vector over the wavelength numbers (1–42), in the spectral range 449–767 nm.

Training a first neural network for pixels classification into classification groups: The profile of all pixels spectra over a selected image, an image of infiltrating-duct-cribriforman tumor in this case (see FIG. 5f), are shown in FIG. 12. In this case, each spectrum is represented as a 42-vector over the spectral range (numbers 1–42 which corroborate 449–767 nm). It is clear that spectra from any other cell image or the combination of more than one image could have been employed.

Figure 13:
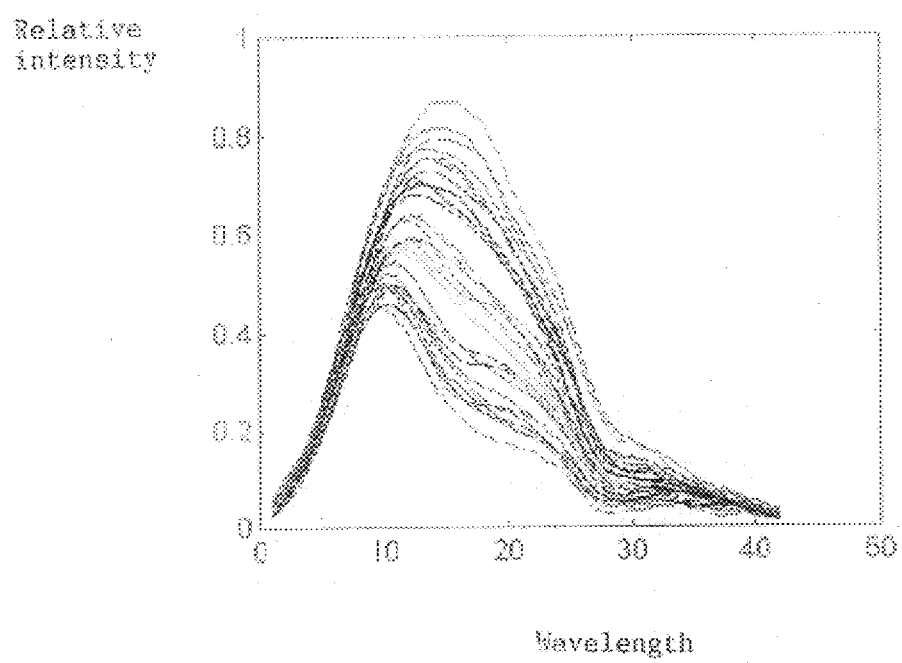
FIG. 13 shows the instruction spectral library used to define six groups of spectra for neural network pixel classification.

Inspecting the spectra presented in FIG. 12, one observes that the spectra are widely spread over the dynamic range (intensity). To create an instructions spectral library for training a net, this range was divided into six classification groups by equally dividing the range into six regions. Each group was thereafter defined by 5 selected representative spectra in the relevant region. These 30 spectra, defining the six groups, are shown in FIG. 13 in six different colors (green, blue, black, yellow, red and light blue), each for a group (designated lateron as groups 1–6, respectively), and form the instructions spectral library for training the neural network. It should be noted that the scope of the present invention is not limited to these specific instructions spectra, and that any other approach for obtaining instructions spectra could have been used. For example, sampling spectra of selected pixels, as described above under Example 2, could have been similarly used.

For training, a two layer neural network was constructed. The input layer consisted of 42 input neurons and the second layer consisted of six output neurons. The network learned to associate each group of instructions spectra (a 42-vector), those shown in FIG. 12, to a predetermined output vector. In this specific example, the first group was associated with the binary vector [100000], the second to [010000] and so on: [001000], [000100], [000010] and [000001]. The learning process was performed using the backpropagation technique. It will be appreciated by one ordinarily skilled in the art that a different number of instructions spectra groups could have been selected, and that the architecture of the network selected accordingly.

A first trained neural network for pixels classification into classification groups: In order to classify each of the pixels in an image into one of the six spectra (classification) groups, each of the cube pixels was run through the trained network (i.e. in which the coupling constants were determined) and the classification group it belongs to, recorded. By assigning an artificial color to each classification group, it was possible to display each spectral cube after classification.

FIGS. 14a–h present the neural network classified images of the cells described under Example 2 above. In this case, however, the classifying network had the option of defining a "non classified" pixel. Its definition depends on the user through a threshold decision. In the images of FIGS. 13a–h, these pixels (very few) appear in black. Pixels associated with classification groups 1–6 appear in red, green, blue, white, yellow and pink, respectively.

For any of the examined cells, high resemblance is observed between images obtained using the conventional classification approach, as for example shown in FIGS. 5a–h (right images), and images obtained using the neural network classification approach, as for example shown in FIGS. 14a–h, respectively. When the term 'classification' is used herein and in the claims with respect to pixels classification it refers to any approach wherein a pixel is classified to a group according to its spectrum.

Following the neural network classification, normalized histograms of each image, as shown in FIGS. 14a–h, were calculated and are presented in FIGS. 15a–h, respectively. These histograms show the relative occupation of pixels belonging to each classified group in a given image. It is clearly noted viewing these histograms that each cell class has a different occupation characteristics of pixels belonging to the classification groups.

Training a second neural network for classification of cancer cells into classes: It should be noted that the histogram of each cube, in the given example, is a 7-vector, the first term of the vector is the relative occupation number of the "not classified" pixels (group 0 in FIGS. 15a–h), the additional 6 terms are the relative occupation numbers of each group (groups 1–7 in FIGS. 15a–h). However, it should be further noted that each cube alternatively may be represented by a vector having less than 7 terms (e.g., 3, 4, 5 or 6 terms), or more. Yet, it should be further noted that classification histograms may alternatively be obtained using the conventional classification approach described hereinabove under Example 2 (see FIGS. 7a–h), which may similarly be represented as vectors.

Figure 14A:
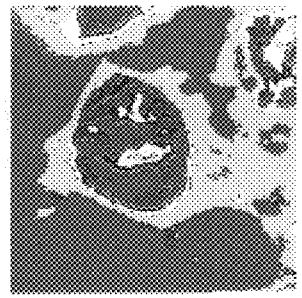
FIGS. 14a–h show classification maps of the cells shown in FIGS. 5a–h, respectively, as obtained using the neural network pixel classification method according to the present invention.
Figure 14E:
Figure 14B:
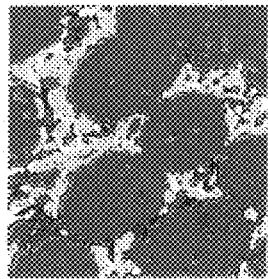
Figure 14F:
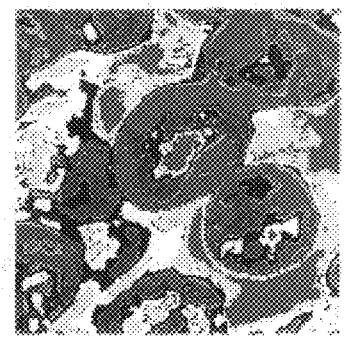
Figure 14C:
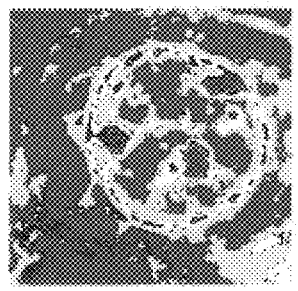
Figure 14G:
Figure 14D:
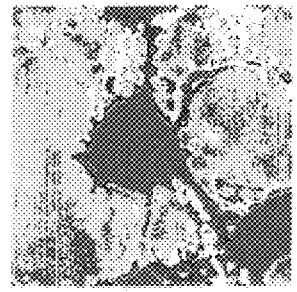
Figure 14H:
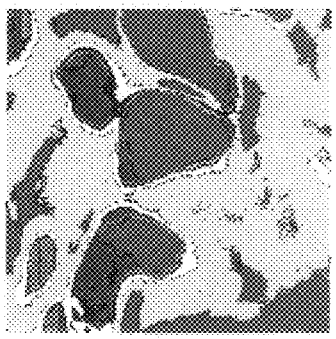
Figure 15A:
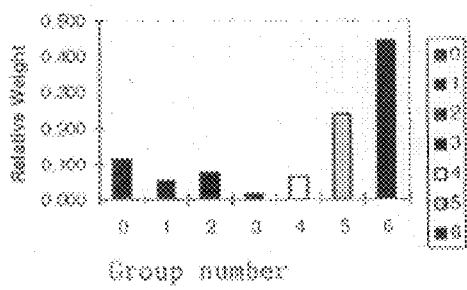
FIGS. 15a–h show abundance histogram s of classified pixels of the images of FIGS. 14a–h, respectively.
Figure 15E:
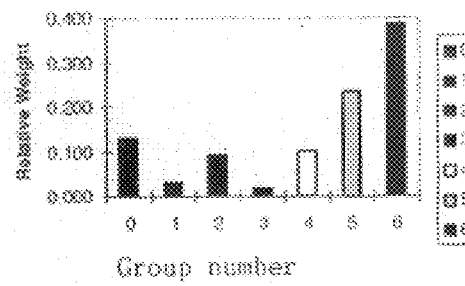
Figure 15B:
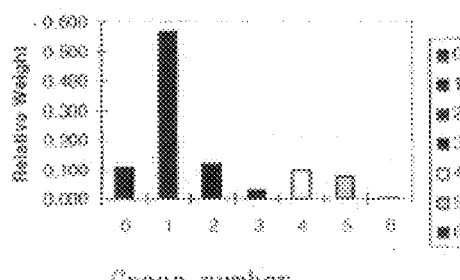
Figure 15F:
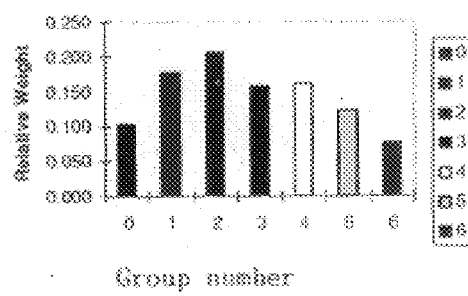
Figure 15C:
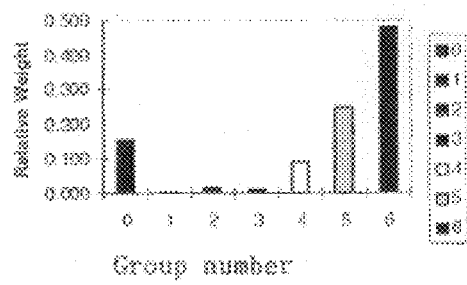
Figure 15G:
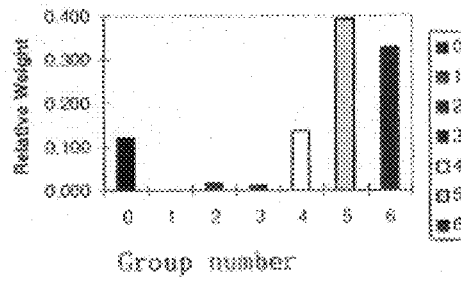
Figure 15D:
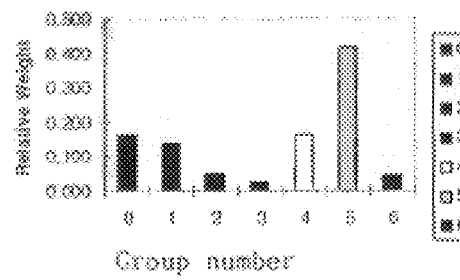
Figure 15H:
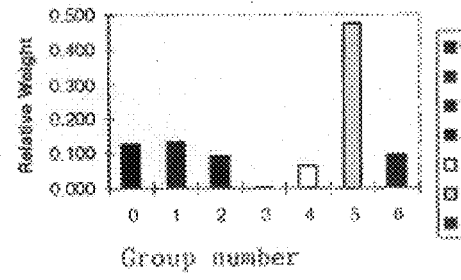

Classification of cancer cells was into 8 classes according to the classes identified independently by pathologists, as described under Examples 1 and 2 above. These included in situ-duct-solid (FIG. 14a, class 1); infiltrating-duct-solid (FIG. 14e, class 2); in situ-duct-cribriform (FIG. 14b, class 3); infiltrating-duct-cribriform (FIG. 14f, class 4); in situ-duct-comedo (FIG. 14c, class 5); infiltrating-duct-comedo (FIG. 14g, class 6); in situ lobular carcinoma (FIG. 14d, class 7); and infiltrating lobular carcinoma (FIG. 14h, class 8).

For training, a two layer neural network was constructed and trained. The input layer consisted of 18 neurons and the second layer consisted of 8 output neurons. These numbers are specific to the given example and may be different, depending on the application. The network learned to associate each instruction histogram (a 7-vector in this case), those shown in FIGS. 15a–h, to a predetermined output binary vector. The first was associated to the binary vector [10000000], the second to [01000000] and so on: [00100000], [00010000], [00001000], [00000100], [00000010] and [00000001]. As before, the learning process was performed using the backpropagation method. It will be appreciated by one ordinarily skilled in the art that a different number of instruction histograms could have been selected for training.

A second neural network for classification of cancer cells into classes: After the net coupling constants were determined during the above described training process, normalized histogram vectors were fed to the network to associate each with a class of the eight cell classes.

In this specific case, the first seven cubes not belonging to the original instruction set which were correctly classified by the network (as compared with the pathologists classification), their data was added to the instruction set to produce better statistics. This procedure should be extended to more cubes in a case that more cubes are to be analyzed, such that the net keeps training every time operated.

The performances of the two cascaded nets was proven excellent. Out of 21 cubes tested, 20 were correctly classified, whereas only one was wrongly classified to class 2.

TABLE 4

| Class | Correctly classified* | Incorrectly classified |
|-------|----------------------|------------------------|
| 1 | 2 | — |
| 2 | 2 | 1 (belongs to class 4)** |
| 3 | 3 | — |
| 4 | 2 | — |
| 5 | 3 | — |
| 6 | 4 | — |
| 7 | 1 | — |
| 8 | 3 | — |

*classification using network corroborated classification of pathologists
**as determined by the pathologists classification Thus, according to the present invention a simple neural network for classification of cells into classes may be devised as follows. First, obtain a number of spectral cubes representing all cell classes. Second, identify the dynamic range of the pixels spectra from one or more cubes. Third, divide this region into a number of required groups (presently 6). The division being equally distributed. Fourth, choose a number of representative pixel spectra for each group (presently 5). Fifth, construct a first two layer neural network (presently, first layer 42 neurons, second layer 6 neurons). Sixth, using the backpropagation method train the net to assign each spectra to its group representative. Seventh, after the net has learned the task, use it to classify each pixel of every new cube to its classification group. For visualization, assign an artificial color to each classification group. Eighth, use the classified images to construct a normalized occupancy histogram for each spectral cube. Ninth, using a number of cubes preclassified into cell classes, construct an instruction set consisting of histogram vectors. Tenth, construct a second two layer neural network (presently, a first layer of 18 neurons and a second layer of 8 neurons). Eleventh, using the backpropagation method, instruct the net to assign each histogram vector to its group representative. Twelfth, upon completion of the training process use the net, to assign histograms of yet unclassified images to its cancer class.

Thus, in examples 1–4, a spectral imaging system was used for classification of standard hematoxylin and eosin breast carcinoma specimens.

Specific patterns of spectra could be correlated with different classes of breast carcinoma cells. Nuclear structure and chromatin condensation in in situ and infiltrating ductal and lobular breast carcinoma were determined.

By classifying each pixel in the examined specimen into a classification group (either by conventional or neural network classifications), the spatial distribution of stained macromolecules possessing similar spectral characteristics are determined and may be analyzed qualitatively and quantitatively, and most importantly, in both cases the analysis is of a more objective nature as compared with prior art approaches.

The present technique has important advantages over the systems already used for image analysis. This is the case since the morphometric image obtained is spectrally categorized into classification groups of similar spectra, which groups represent morphological features used in morphometric analysis in a more comprehensive and meaningful way.

In the broad sense, according to the present invention provided is a new method for classification of cells into classes by identification and classification of spectral parameters, since different patterns of spectra are related to different classes of cells. The method can thus be used for classification of cells to developmental stages, and to qualify and quantify metabolic processes within cells.

One of the major benefits of the present invention will be the establishment of quantitative indexes for classification and grading of neoplasms. These indexes will provide a quantitative reference for classification based on spectrally resolved morphometric data, and will enable refined diagnosis and prognosis, both may affect choice of treatment. It will further affect treatment of patients in cases where stage (grade) specific treatment is of choice. It is important to note in this context that it is well established that morphometric analyses are of great importance in the classification of many neoplasms. The method of the present invention was herein demonstrated for breast cancer, yet it is clear that the method may be implemented to a similar extent with respect to other types of neoplasm including other carcinomas, sarcomas, leukemias, lymphomas, and the like, since all of these neoplasms are currently classified according to conventional morphometric analysis.

While the invention has been described with respect to a limited number of embodiments, it will be appreciated that many variations, modifications and other applications of the invention may be made.

What is claimed is:

1. A spectral bio-imaging method for cells classification into classes, the method comprising the steps of:
   (a) preparing a sample to be spectrally imaged, said sample including at least a portion of at least one cell;
   (b) viewing said sample through an optical device, said optical device being optically connected to an imaging spectrometer, said optical device and said imaging spectrometer being for obtaining a spectrum of each pixel of said sample;
   (c) classifying each of said pixels into classification groups according to said pixels spectra; and
   (d) analyzing said classification groups and thereby classifying said at least one cell into a cell class.

2. A method as in claim 1, wherein said preparation of step (a) involves staining said cell via a staining method selected from the group consisting of Haematoxylin-Eosin staining, Giemsa staining, mason tricolor staining and papanicolaou staining.

3. A method as in claim 1, wherein said obtainment of said spectrum of each pixel of step (b) is effected by:
   (i) collecting incident light simultaneously from all pixels of said sample using collimating optics;
   (ii) passing said incident collimated light through an interferometer system having a number of elements, so that said light is first split into two coherent beams which travel in different directions inside said interferometer and then said two coherent beams recombine to interfere with each other to form an exiting light beam;
   (iii) passing said exiting light beam through a focusing optical system which focuses said exiting light beam on a detector having a two-dimensional array of detector elements, so that at each instant each of said detector elements is the image of one and always the same pixel of said sample for the entire duration of the measurement, so that the real image of the sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
   (iv) scanning one or more of said elements of said interferometer system, so that said optical path difference between said two coherent beams generated by said interferometer system is scanned simultaneously for all said pixels of said sample; and
   (v) recording signals of each of said detector elements as function of time using a recording device to form a spectral cube of data.

4. A method as in claim 1, wherein said optical device is a microscope.

5. A method as in claim 1, wherein said imaging spectrometer includes an element selected from the group consisting of a dispersion element, a filter and an interferometer.

6. A method as in claim 1, wherein pixels classified to a classification group via said classification of step (c) are presented in an image by a preselected artificial color.

7. A method as in claim 1, wherein pixels classified to a classification group via said classification of step (c) are presented as an abundance histogram.

8. A method as in claim 1, wherein said abundance histogram is relative.

9. A method as in claim 7, wherein said abundance histogram serves for said classification of said at least one cell into said cell class of step (d).

10. A method as in claim 1, wherein said classification of each of said pixels into said classification groups according to said pixels spectra of step (c) is effected using a classification map algorithm which employs reference spectra for associating pixels into said classification groups.

11. A method as in claim 10, wherein said reference spectra for classification are of a previously prepared reference library.

12. A method as in claim 10, wherein at least one of said reference spectra for classification is of pixels derived from a cell domain selected from the group consisting of nucleolus, inter-chromosomal region, cytoplasm, a first chromatin region of the nucleus, a second chromatin region of the nucleus and background.

13. A method as in claim 10, wherein pixels classified to a classification group via said classification map algorithm are presented in an image by a preselected artificial color.

14. A method as in claim 10, wherein pixels classified to a classification group via said classification map algorithm are presented as an abundance histogram.

15. A method as in claim 14, wherein said abundance histogram serves for said classification of said at least one cell into said cell class of step (d).

16. A method as in claim 15, wherein said abundance histogram serves for said classification of said at least one cell into said cell class of step (d) via a trained neural network algorithm which associates abundance histogram s with cell classes.

17. A method as in claim 1, wherein said classification of each of said pixels into said classification groups according to said pixels spectra of step (c) is effected using a first trained neural network algorithm which associates a pixel into a classification group according to said pixel's spectrum.

18. A method as in claim 17, wherein pixels classified to a classification group via said first trained neural network algorithm are presented in an image by a preselected artificial color.

19. A method as in claim 17, wherein pixels classified to a classification group via said first trained neural network algorithm are presented as an abundance histogram.

20. A method as in claim 19, wherein said abundance histogram serves for said classification of said at least one cell into said cell class of step (d) via a second trained neural network algorithm which associates abundance histogram s with cell classes.

21. A method as in claim 1, wherein said cell is a cancer cell.

22. A method as in claim 21, wherein said cancer is selected from the group consisting of carcinoma, sarcoma, leukemia and lymphoma.

* * * * *